(12) United States Patent
Gomer et al.

(10) Patent No.: US 7,763,256 B2
(45) Date of Patent: *Jul. 27, 2010

(54) COMPOSITIONS AND METHODS FOR SUPPRESSING FIBROCYTES AND FOR DETECTING FIBROCYTE DIFFERENTIATION

(75) Inventors: Richard Gomer, Houston, TX (US); Darrell Pilling, Pearland, TX (US)

(73) Assignee: William Marsh Rice University, Houston, TX (US)

( * ) Notice: Subject to any disclaimer, the term of this patent is extended or adjusted under 35 U.S.C. 154(b) by 440 days.

This patent is subject to a terminal disclaimer.

(21) Appl. No.: 11/535,636

(22) Filed: Sep. 27, 2006

(65) Prior Publication Data

US 2007/0065368 A1 Mar. 22, 2007

Related U.S. Application Data

(63) Continuation-in-part of application No. 11/158,966, filed on Jun. 22, 2005, now Pat. No. 7,666,432, which is a continuation-in-part of application No. PCT/US03/40957, filed on Dec. 22, 2003.

(60) Provisional application No. 60/436,046, filed on Dec. 23, 2002, provisional application No. 60/436,027, filed on Dec. 23, 2002, provisional application No. 60/515,776, filed on Oct. 30, 2003, provisional application No. 60/519,467, filed on Nov. 12, 2003, provisional application No. 60/525,175, filed on Nov. 26, 2003.

(51) Int. Cl.
*A61K 38/00* (2006.01)
*C07K 7/00* (2006.01)
*C07K 14/00* (2006.01)

(52) U.S. Cl. .................. 424/198.1; 514/2; 530/350
(58) Field of Classification Search ................ None
See application file for complete search history.

(56) References Cited

U.S. PATENT DOCUMENTS

| | | | | |
|---|---|---|---|---|
| 4,233,969 A | 11/1980 | Lock et al. | .................. | 128/156 |
| 4,782,014 A | 11/1988 | Serban et al. | .................. | 435/7 |
| 5,092,876 A | 3/1992 | Dhawan et al. | .............. | 623/11 |
| 5,654,186 A | 8/1997 | Cerami et al. | .............. | 435/325 |
| 5,698,589 A | 12/1997 | Allen | ..................... | 514/509 |
| 5,804,446 A | 9/1998 | Cerami et al. | .............. | 435/385 |
| 5,846,796 A | 12/1998 | Cerami et al. | ............ | 435/172.3 |
| 6,037,458 A | 3/2000 | Hirai et al. | .................. | 530/415 |
| 6,054,121 A | 4/2000 | Cerami et al. | .............. | 424/93.7 |
| 6,126,918 A | 10/2000 | Pepys et al. | .................. | 424/9.1 |
| 6,174,526 B1 | 1/2001 | Cerami et al. | .............. | 424/93.1 |
| 6,365,570 B1 | 4/2002 | Van Kessel et al. | ........... | 514/8 |
| 6,406,698 B1 | 6/2002 | Svehag et al. | ............ | 424/184.1 |
| 6,537,811 B1 | 3/2003 | Freier | ..................... | 435/375 |
| 6,600,019 B2 | 7/2003 | Prayaga et al. | .............. | 530/350 |
| 6,872,541 B2 | 3/2005 | Mills | .................. | 435/7.21 |
| 2002/0058284 A1 | 5/2002 | Winkel | .................. | 435/7.1 |
| 2003/0003567 A1 | 1/2003 | Barber et al. | ............ | 435/235.1 |
| 2003/0022245 A1 | 1/2003 | Mills | .................. | 435/7.8 |
| 2004/0068095 A1 | 4/2004 | Shimkets et al. | ........... | 530/350 |
| 2005/0238620 A1 | 10/2005 | Gomer et al. | .............. | 424/85.2 |

FOREIGN PATENT DOCUMENTS

| | | |
|---|---|---|
| WO | 9941285 | 8/1999 |
| WO | 03031572 | 4/2003 |
| WO | 03097104 | 11/2003 |
| WO | 2004058292 | 12/2003 |
| WO | 2004059318 | 12/2003 |
| WO | 2004016750 | 2/2004 |
| WO | 2004059318 | 7/2004 |
| WO | 2005110474 | 11/2005 |
| WO | 2005115452 | 12/2005 |
| WO | 2006002438 | 1/2006 |

OTHER PUBLICATIONS

Ashcroft et al., "Simple Method of Estimating Severity of Pulmonary Fibrosis on a Numerical Scale", J Clin Pathol 41, pp. 467-470, 1988.
Ashikawa et al., "Piceatannol Inhibits TNF-Induced NF-KappaB Activation and NF-KappaB-Mediated Gene Expression Through Suppression of IkappaBalpha Kinase and p65 Phosphorylation", The Journal of Immunology, 169, (pp. 6490-6497), 2002.
Bain et al., "The Specificities of Protein Kinase Inhibitors: An Update", Biochem. Journal, 371, (pp. 199-204), 2003.
Brown, "The role of extracellular matrix proteins in the control of phagocytosis", Journal of Leukocyte Biology, vol. 39, (pp. 579-591), 1986.
Crouch, E., "Patholbiology of Pulmonary Fibrosis", Am J Physiol Lung Cell Mol Physiol 259, pp. L159-L184, 1990.
De Beer et al., "Isolation and Characterization of C-Reactive Protein and Serum Amyloid P Component in the Rat", Immunology 45, pp. 55-70, 1982.
Duchemin et al., "Association of Non-Receptor Protein Tyrosine Kinases with the Fc Gamma RI/Gamma-Chain Complex in Monocytic Cells", The Journal of Immunology, 158, (pp. 865-871), 1997.
Du Clos, et al., "Reply to Human C-reactive protein does not bind to fc gamma RIIa on phagocytic cells", The Journal of Clinical Investigation, vol. 107, No. 5, pp. 643, 2001.

(Continued)

*Primary Examiner*—Prema Mertz
(74) *Attorney, Agent, or Firm*—Baker Botts L.L.P.

(57) ABSTRACT

The present invention relates to the ability of SAP to suppress fibrocytes. It also relates to the ability of IL-12, laminin-1, cross-linked IgG and IgG aggregates to suppress fibrocytes. Methods and compositions for suppressing fibrocytes using these proteins are provided. These methods are useful in a variety of applications including treatment and prevention of fibrosing diseases such as scleroderma, pulmonary fibrosis and asthma. Finally, the invention includes assays for detecting the ability of various agents to modulate differentiation into fibrocytes. Such assays may also be used to diagnose scleroderma, pulmonary fibrosis, or other fibrosing diseases.

13 Claims, 19 Drawing Sheets

OTHER PUBLICATIONS

Emsley et al., "Structure of Pentameric Human Serum Amyloid P Component", Nature 367, pp. 338-345, 1994.
Ghazizadeh et al., "Physical and Fuctional Association of Src-Related Protein Tyrosine Kinases with Fc Gamma-RII in Monocytic THP-1 Cells", The Journal Of Biological Chemistry, vol. 269, No. 12, (pp. 8878-8884), 1994.
Grazia, et al., "Suppression of IL-12 Transcription in Macrophages Following Fc Receptor Ligation", The Journal of Immunology, vol. 166, (pp. 4498-4506), 2001.
Gregory et al., "The DNA Sequence and Biological Annotation of Human Chromosome 1", Nature 441, pp. 315, 2006.
Hohenester et al., "Crystal Structure of a Decameric Complex of Human Serum Amyloid P Component with Bound dAMP", J. Mol. Biol. 269, pp. 570-578, 1997.
Huang et al., "The Monocyte Fcgamma receptors FcgammaRI/gamma and FcgammaRIIA Differ in their Interaction with Syk and with Src-Related Tyrosine Kinases", Journal of Leukocyte Biology, vol. 76, (pp. 491-499), 2004.
International Search Report or (Examination Report) for European Patent Application No. 03 800 146.7 (5 pages), 2007.
International Search Report, PCT/US2006/005229, 33 pages, 2007.
Junqueira et al., "Picrosirius Straining Plus Polarization Microscopy, a Specific Method for Collagen Detection in Tissue Sections", Histochem. J 11, pp. 447-455, 1979.
Kiernan et al., "Proteomic Characterization of Novel Serum Amyloid P Component Variants from Human Plasma and Urine", Proteomics 4, (pp. 1825-1829), 2004.
Kisseleva et al., Bone Marrow-Derived Fibrocytes Participate in Pathogenesis of Liver Fibrosis, 45 Journal of Hepatology, pp. 429-438, 2006.
Korade-Mirnics et al., "Src Kinase-Mediated Signaling in Leukocytes", Journal of Leukocyte Biology, vol. 68, (pp. 603-613), 2000.
Lai et al., "Potent Small Molecule Inhibitors of Spleen Tyrosine Kinase (Syk)", Bioorganic & Medicinal Chemistry Letters 13, (pp. 3111-3114), 2003.
Lei et al., "Genomic DNA Sequence for Human C-Reactive Protein", J. Biol. Chem. 260, pp. 13377-13383, 1985.
Lindenbaum et al., "Serum-Free Cell Culture Medium Induces Acceleration of Wound Healing in Guinea-Pigs", Burns, vol. 21, No. 2 (pp. 110-115), 1995.
Liu et al., "Human Plasma N-Glycoproteome Analysis by Immunoaffinity Subtraction, Hydrazide Chemistry, and Mass Spectrometry", J. Proteome Res. 4, pp. 2070-2080, 2005.
Mantzouranis et al., "Human Serum Amyloid P Component", cDNA Isolation, Complete Sequence of Pre-Serum Amyloid P Component, and Localization of the Gene to Chromosome, The Journal of Biological Chemistry, vol. 260, No. 12, pp. 7752-7756, 1985.
Murphy et al., "Extrahepetic Transcription of Human C-Reactive Protein", Journal of Experimental Medicine, vol. 73, (pp. 495-498), 1991.
Ohnishi et al., "Isolation and Characterization of the Complete Complementary and Genomic DNA Sequences of Human Serum Amyloid P Component", J. Biochem. 100, pp. 849-858, 1986.
Oliveira et al., "Primary Structure of Human C-Reactive Protein", The Journal of Biological Chemistry, vol. 254, No. 2, (pp. 489-502), 1979.
Oriente et al., "Interleukin-13 Modulates Collagen Homeostasis in Human Skin and Keloid Fibroblasts", The Journal of Pharmacology and Experimental Therapeutics, vol. 292, No. 3 (pp. 988-994), 2000.
Osmand et al., Partial Amino-Acid Sequences of Human and Rabbit C-Reactive Proteins: Homology with Immunoglobulins and Histocompatibility AntigensProc. Natl. Acad. Sci. U.S.A. vol. 74, No. 3, (pp. 1214-1218), 1977.
Pachence, et al., "Tissue-Activated Delivery—Novel Methods for Site-Directed Drug Delivery", Drug Delivery Technology, vol. 3, No. 1, (pp. 40-45), 2003.
Pepys et al., "Human Serum Amyloid P Component is an Invariant Constituent of Amyloid Deposits and has a Uniquely Homogeneous Glycostructure", Proc. Natl. Acad. Sci. U.S.A., vol. 91, (pp. 5602-5606), 1994.

Pontet, et al., "One step preparation of both human C-reactive protein and CIt", FEBS Letters, vol. 88, No. 2, pp. 172-175, 1978.
Prelli et al., "The Primary Structure of Human Tissue Amyloid P Component From A Patient with Primary Idiopathic Amyloidosis", The Journal of Biological Chemistry, vol. 260, No. 24, (pp. 12895-12898), 1985.
Russo et al., "Liver Fibrosis; Bone Marrow Functionality Contributes to Liver Fibrosis", 130(6) Gastroenterology Week Jul. 31, 2006, (pp. 83-84), 2006.
Sada et al., "Structure and Function of Syk Protein-Tyrosine Kinase", The Japanese Biochemical Society, vol. 130, No. 2, (pp. 177-186), 2001.
Shrive et al., "Three Dimensional Structure of Human C-Reactive Protein", Nature Structural Biology, vol. 3, No. 4, (pp. 346-353), 1996.
Sjoeblom et al., "The Consensus Coding Sequences of Human Breast and Colorectal Cancers", Science vol. 314, www.sciencemag.org, (pp. 268-274), 2006.
Srinivasan et al., "Comparative Analyses of Pentraxins: Implications for Protomer Assembly and Ligand Binding", Structure, vol. 2, No. 11, (pp. 1017-1027), 1994.
Su et al., "Distinct Mechanisms of STAT Phosphorylation Via the Interferon-Alpha/Beta Receptor—Selective Inhibition of STAT3 and STAT5 by Piceatannol", The Journal of Biological Chemistry, vol. 275, No. 17 (pp. 12661-12666), 2000.
The MGC Project Team, "The Status, Quality, and Expansion of the NIH Full-Length cDNA Project: The Mammalian Gene Collection (MGC)", Genome Research, 14, pp. 2121-2127, 2004.
Thompson et al., "Human Plasma P Component: Isolation and Characterization", Biochemistry, vol. 17, No. 20, (pp. 4304-4311), 1978.
Thompson et al., "The Physiological Structure of Human C-Reactive Protein and its Complex with Phosphocholine", Structure, vol. 7, No. 2, (pp. 169-177), 1999.
Tridandapani et al., "Regulated Expression and Inhibitory Function of FcgammaRIIb in Human Monocytic Cells", The Journal of Biological Chemistry, vol. 277, No. 7, (pp. 5082-5089), 2002.
Tucci et al., "Biosynthesis and Postsynthetic Processing of Human C-Reactive Protein", The Journal of Immunology, vol. 131, No. 5, pp. 2416-2419, 1983.
Turner et al., "Tyrosine Kinase SYK: Essential Functions for Immunoreceptor Signalling", Review Immunology Today, vol. 21, No. 3 (pp. 148-154), 2000.
Underwood et al., SB 239063, "A p38 MAPK Inhibitor, reduces Neutrophilia, Infamatory Cytokines, MMP-9, and Fibrosis in Lung", Am J Physiol Lung Cell Mol Physiol, vol. 279, pp. L895-L902, 2000.
Vidal et al., "Inducible expression of PTX3, a new member of the pentraxin family, in human mononuclear phagocytes", Blood, vol. 84, No. 10, (pp. 3483-3493), 1994.
Whitehead et al., "Isolation of Human C-Reactive Protein Complementary DNA and Localization of the Gene to Chromosome 1", Science, vol. 221, No. 4605, pp. 69-71. http://www.jstor.org/stable/1691455, 1983.
Woo et al., "Characterization of Genomic and Complementary DNA Sequence of Human C-Reactive Protein, and Comparison with the Complementary DNA Sequence of Serum Amyloid P Component", The Journal of Biological Chemistry, vol. 260, No. 24, (pp. 13384-13388), 1985.
Zheng et al., "Piceatannol, a Stilbene Phytochemical, Inhibits Mitochondrial F0F1-ATPase Activity by Targeting the F1 Complex", Biochemical And Biophysical Research Communications, vol. 261, No. 2, (pp. 499-503), 1999.
International Search Report, PCT/US2003/041183, 5 pages, 2004.
International Search Report, PCT/US2003/040957, 7 pages, 2004.
European Office Action; Application No. 03 814 319.4-2404; pp. 8, Apr. 21, 2009.
Australian Office Action; Application No. 2003299873; pp. 2, Apr. 23, 2009.
PCT International Search Report Application No. PCT/US03/40957 mailed Sep. 16, 2004 (12 pages).
PCT International Search Report Application No. PCT/US2006/005229 Mailed Oct. 31, 2006 (14 pages).
Communication in European Patent Application No. 03 814 319.4 dated Sep. 26, 2008 (4 pages).

Response to Communication in European Patent Application No. 03 814 319.4 dated Mar. 23, 2009 (8 Pages).

Communication in European Patent Application No. 03 814 319.4 dated Apr. 21, 2009 (4 pages).

Response to Communication in European Patent Application No. 03 814 319.4 dated Sep. 28, 2009 (8 pages).

Examiner's First Report on Australian Patent Application No. 2003300266 dated May 21, 2008 (2 pages).

Request to Amend in Australian Patent Application No. 2003300266 dated Aug. 21, 2009 (13 pages).

F.C. de Beer et al., "Fibronectin and C4-Binding Protein are Selectively Bound by Aggregated Amyloid Component", The Rockefeller University Press, vol. 154, pp. 1134-1149, Oct. 1981.

Lawrence A. Potempa et al., "Effect of Divalent Metal Ions and pH Upon the Binding Reactivity of Human Serum Amyloid P Component, a C-Reactive Protein Homologue, for Zymosan", The Journal of Biological Chemistry, vol. 260, pp. 12142-12147, Oct. 5, 1985.

Terry W. Du Clos, "C-Reactive Protein Reacts With the U1 Small Nuclear Ribonucleoprotein", The Journal of Immunology, vol. 143, pp. 2553-2559, Oct. 15, 1989.

Marilyn R. Brown et al., "Receptor-Ligand Interactions Between Serum Amyloid P Component and Model Soluble Immune Complexes", The Journal of Immunology, vol. 151, pp. 2087-2095, Aug. 15, 1993.

Lorraine L. Marnell et al., "C- Reactive Protein Binds to FcγRI in Transfected COS Cells", The American Association of Immunologists, 9 Pgs., Feb. 22, 1995.

Annalisa D'Andrea et al., "Stimulatory and Inhibitory Effects of Interleukin (IL)-4 and IL-13 on the Production of Cytokines by Human Peripheral Blood Mononuclear Cells: Priming for IL-12 and Tumor Necrosis Factor α Production", The Rockefeller University Press, vol. 181, pp. 537-546, Feb. 1995.

Kamyar Zahedi, "Characterization of the Binding of Serum Amyloid P to Type IV Collagen", The Journal of Biological Chemistry, vol. 271, No. 25, pp. 14897-14902, Jun. 21, 1996.

Marc Daëron, "Fc Receptor Biology", www.arjournals.annualreviews.org , pp. 203-234, 1997.

Kamyar Zahedi, "Characterization of the Binding of Serum Amyloid P to Laminin", The Journal of Biological Chemistry, vol. 272, No. 4, pp. 2143-2148, Jan. 24, 1997.

Carla J.C. de Haas et al., "A Synthetic Lipopolysaccharide-Binding Peptide Based on Amino Acids 27-39 of Serum Amyloid P Component Inhibits Lipopolysaccharide-Induced Responses in Human Blood", The Journal of Immunology, pp. 3607-3615, 1998.

Dwaipayan Bharadwaj et al., "The Major Receptor for C-Reactive Protein on Leukocytes Is Fcγ Receptor II", The Journal of Experimental Medicine, vol. 190 No. 4, pp. 585-590, Aug. 16, 1999.

M.C.M. Bickerstaff et al., "Serum Amyloid P Component Controls Chromatin Degration and Prevents Antinuclear Autoimmunity", Nature Medicine, vol. 5, No. 6, pp. 694-697, Jun. 1999.

Fayyaz S. Sutterwala et al., "The Taming of IL-12 Suppressing the production of Proinflammatory Cytokines", Journal of Leukocyte Biology, vol. 65, pp. 543-551, May 1999.

Richard F. Mortensen et al., "Regulation of Phagocytic Leukocyte Activities by C-reactive Protein", Journal of Leukocyte Biology, vol. 67, pp. 495-500, Apr. 2000.

Mary-Pat Stein et al., "C-reactive Protein Binding to FcγRIIa on Human Monocytes and Neutrophils is Allele-Specific", The Journal of Clinical Investigation, vol. 105, pp. 369-376, Feb. 2000.

Dwaipayan Bharadwaj et al., "Serum Amyloid P Component Binds to Fcγ Receptors and Opsonizes Particles for Phagocytosis", The Journal of Immunology, vol. 166, pp. 6735-6741, 2001.

Eirikur Saeland et al., "Human C-reactive Protein Does not Bind to FcγRIIa on Phagocytic Cells", The Journal of Clinical Investigation, vol. 107 No. 5, pp. 641-643, Mar. 2001.

Carolyn Mold et al., "Serum Amyloid P Component and C-Reactive Protein Mediate Phagocytosis Through Murine FcγRs", The Journal of Immunology, vol. 166, pp. 1200-1205, 2001.

Katherine B. Bodman-Smith et al., "C-Reactive Protein-Mediated Phagocytosis and Phospholipase D Signalling Through the High-Affinity Receptor for Immunoglobulin G (FcγRI)", The Journal of Immunology, vol. 107 No. 2, pp. 252-260, Oct. 2002.

Matthias Schmidt et al., "Identification of Circulating Fibrocytes as Precursors of Bronchial Myofibroblasts in Asthma", The Journal of Immunology, vol. 170, pp. 380-389, Apr. 22, 2003.

Liju Yang et al., "Peripheral Blood Fibrocytes From Burn Patients: Identification and Quantification of Fibrocytes in Adherent Cells Cultured From Peripheral Blood Mononuclear Cells", Laboratory Investigation, vol. 82, No. 9, pp. 1183-1192, Apr. 15, 2002.

Thomas A. Wynn, "IL-13 Effector Functions", www.arjournals.annualreviews.org , pp. 425-456, 2003.

Roderick J. Philips et al., "Circulating Fibrocytes Traffic to the Lungs in Response to CXCL 12 and Mediate Fibrosis", The Journal of Clinical Investigation, vol. 114, No. 3, pp. 438-446, Aug. 2004.

Bethany B. Moore et al., "CCR2-Mediated Recruitment of Fibrocytes to the Alveolar Space After Fibrotic Injury", American journal of Pathology, vol. 166, No. 3, pp. 675-684, Mar. 2005.

Luca Mori et al., "Fibrocytes Contribute to the Myofibroblast Population in Wounded Skin and Originate From the Bone Marrow", www.sciencedirect.com , pp. 81-90, Aug. 10, 2004.

Liju Yang, PhD et al., "Identification of Fibrocytes in Postburn Hypertrophic Scar", Wound Repair and Regeneration, vol. 13, No. 4, pp. 398-404, Jan. 17, 2005.

Riichiro Abe et al., "Peripheral Blood Fibrocytes: Differentaion Pathway and Migration to Wound Sites", The Journal of Immunology, vol. 166, pp. 7556-7562, 2001.

Jason Chesney et al., "The Peripheral Blood Fibrocyte is a Potent Antigen-Presenting Cell Capable of Priming Naive T Cells in Situ", Journal of Immunology, vol. 94, pp. 6307-6312, Jun. 1997.

Darrell Pilling et al., "Inhibition of Fibrocyte Differentation by Serum Amyloid P1", The Journal of Immunology, vol. 171, pp. 5537-5546, 2003.

C.N. Metz, "Fibrocytes: A unique Cell Population Implicated in Wound Healing", Cell. Mol. Life Sci., vol. 60, pp. 1342-1350, Jan. 16, 2003.

R. Bucala et al., "Circulating Fibrocytes Define a New Leukocyte Subpopulation That Mediates Tissue Repair", Molecular Medicine, vol. 1, No. 1, pp. 71-81, Nov. 1994.

J. Chesney et al., "Peripheral Blood Fibrocytes: Mesenchymal Precursor Cells and the Pathogenesis of Fibrosis", Curr.Rheumatol.Rep 2:501-505, 2000.

J. Chesney et al., "Regulated Production of Type I Collagen and Inflammatory Cytokins by Peripheral Blood Fibrocytes", The Journal of Immunology, pp. 15, 1998.

M. Chi et al., "C-Reactive Protein Induces Signaling Through FcγRIIa on HL-60 Granulocytes", The Journal of Immunology, pp. 1413-1418, 2002.

R.B. Christner et al., "Binding of Human Serum Amyloid P-Component to Phosphocholine", Archives of Biochemistry and Biophysics, vol. 314, No. 2, pp. 337-343, Nov. 1, 1994.

Richard A.F. Clark, "Fibrin and Wound Healing", Annals New York Academy of Sciences 936, pp. 355-367, 2001.

Marc Daëron, "Structural Bases of FcγR Functions", Int.Rev.Immunol. 16:1-27, 1997.

F.C. De Beer et al., "Isolation of Human C-Reactive Protein and serum Amyloid P Component", Journal of Immunological Methods, pp. 17-31, 1982.

E. Saeland et al., "Human C-Reactive Protein Does not Bind to FcγRIIa on Phagocytic Cells", The Journal of Clinical Investigation, vol. 107, No. 5, pp. 641-643, Mar. 2001.

H. Gewurz et al., "Structure and Function of the Pentraxins", Current Opinion in Immunology, vol. 7, pp. 54-64, 1995.

M.G. Cappiello et al., "Suppression of IL-12 Transcription in Macrophages Following Fcγ Receptor Ligation", The Journal of Immunology, vol. 166, pp. 4498-4506, 2001.

Ingo Hartlapp et al., "Fibrocytes Induce an Angiogenic Phenotype in Cultured Endothelial Cells and Promote Angiogenesis in Vivo", The FASEB Journal, vol. 15, pp. 2215-2224, Oct. 2001.

Niels H.H. Heegaard et al., "Ligand-Binding Sites in Human Serum Amyloid P Component", Eur.J.Biochem. 239:850-856, 1996.

Charles R.K. Hind et al., "Human Serum Amyloid P Component, a Circulating Lectin with Specificity for the Cyclic 4,6-Pyruvate Acetal of Galactose: Interaction with Varous Bacteria", Biochem.J. 225:107-111, 1985.

Winston L. Hutchinson et al., "Human Serum Amyloid P Component is a Single Uncomplexed Pentamer in Whole Serum", Molecular Medicine, vol. 6, No. 6, pp. 482-493, 2000.

Guido Majno, "Chronic Inflammation: Links With Angiogenesis and Wound Healing", American Journal of Pathology, vol. 153, No. 4, pp. 1035-1039, Oct. 1998.

M.B. Pepys et al., "Serum Amyloid P Component is the Major Calcium-Dependent Specific DNA Binding Protein of Serum", Biochemical and Biophysical Research Communications, vol. 148, No. 1, pp. 208-313, Oct. 14, 1987.

M.B. Pepys et al., "Amyloid P Component. ACritical Review", Amyloid: Int. J. Exp. Invest., vol. 4, pp. 274-295, 1997.

Diana M. Steel et al., "The Major Acute Phase Reactants: C-Reactive Protein, Serum Amyloid P Component and Serum Amyloid A Protein", Immunology Today, vol. 15, No. 2, pp. 81-88, 1994.

Giorgio Trinchieri, "Interleukin-12 and the Regulation of Innate Resistance and Adaptive Immunity", Nature Reviews Immunology, vol. 3, pp. 133-146, Feb. 2003.

John E. Volanakis, "Human C-Reactive Protein: Expression, Structure, and Function", Molecular Immunology, vol. 28, pp. 189-197, 2001.

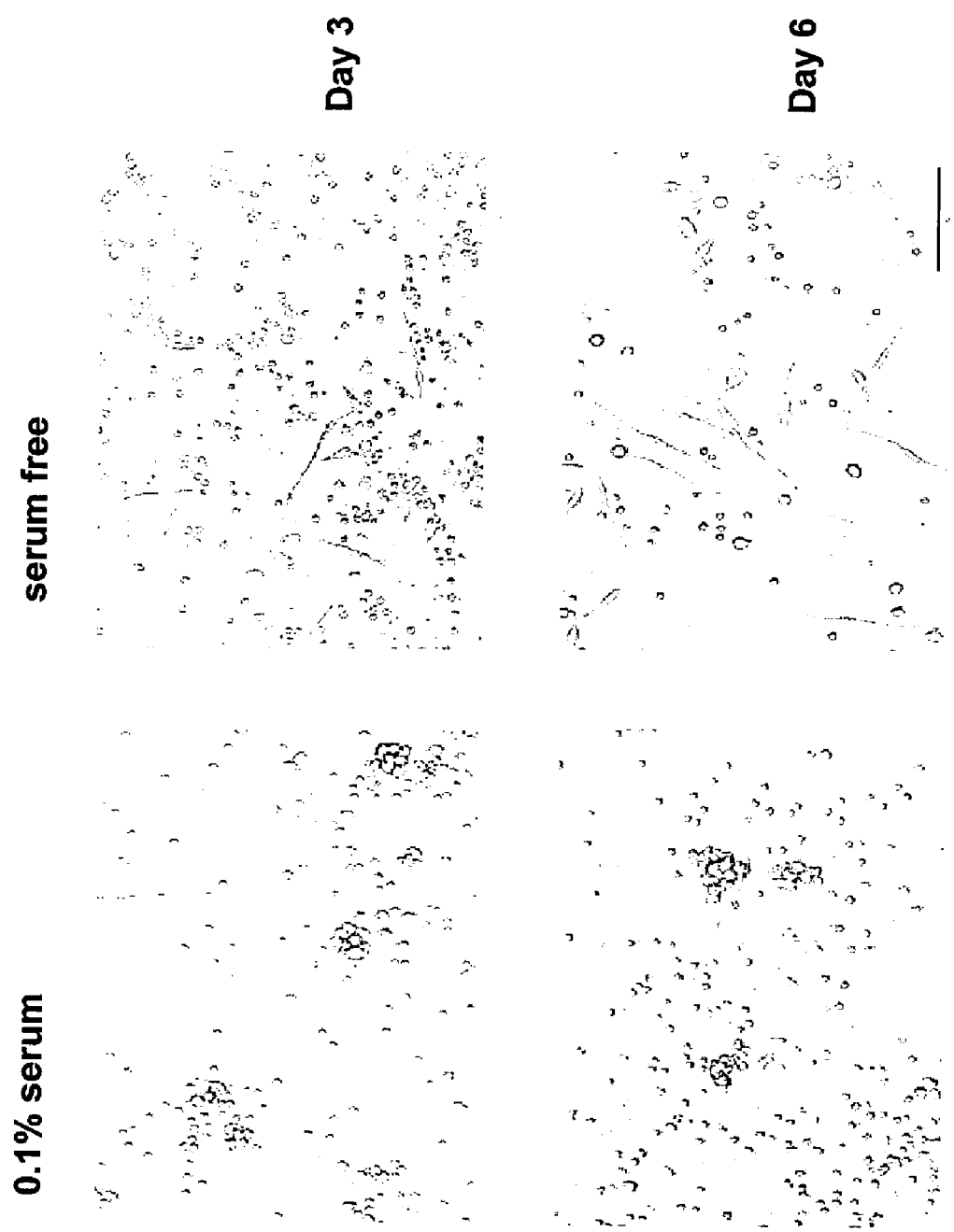

ative hypothesis is that circulating fibroblast precursors (called fibrocytes) present within the blood migrate to the sites of injury or fibrosis, where they differentiate and mediate tissue repair and other fibrotic responses.
COMPOSITIONS AND METHODS FOR SUPPRESSING FIBROCYTES AND FOR DETECTING FIBROCYTE DIFFERENTIATION

PRIORITY CLAIM

The present application is a continuation-in-part of U.S. application Ser. No. 11/158,966 filed Jun. 22, 2005, and now U.S. Pat. No. 7,666,432; which is a continuation-in-part under 35 U.S.C. §120 of PCT patent application serial number PCT/US2003/040957, filed Dec. 22, 2003 and titled "Methods and Conditions for Suppressing Fibrocyte Differentiation", published in English as WO 2004/058292 on Jul. 15, 2004; which claims priority to the following: U.S. Provisional Patent Applications: U.S. 60/436,046, filed Dec. 23, 2002; U.S. 60/436,027, filed Dec. 23, 2002; U.S. 60/515,776, filed Oct. 30, 2003; U.S. 60/519,467, filed Nov. 12, 2003; and U.S. 60/525,175 filed Nov. 26, 2003. Pertinent parts of all above applications are incorporated by reference herein.

TECHNICAL FIELD

The present invention relates to the ability of SAP, IL-12, Laminin-1, IgG aggregates, and/or cross-linked IgG to suppress fibrocytes. Accordingly, it may include compositions and methods for suppressing fibrocytes. These compositions and methods may be useful in a variety of applications, for example, those in which decreased fibrocyte formation is beneficial, such as treatment of fibrosing diseases and asthma. The invention may additionally include methods for detecting problems in fibrocyte proliferation or differentiation, or for SAP, IL-12, Laminin-1, IgG aggregates, and/or cross-linked IgG to inhibit this proliferation or differentiation. These problems may be correlated with a disease or may be drug-induced.

BACKGROUND

Fibrocytes

Inflammation is the coordinated response to tissue injury or infection. The initiating events are mediated by local release of chemotactic factors, platelet activation, and initiations of the coagulation and complement pathways. These events stimulate the local endothelium, promoting the extravasation of neutrophils and monocytes. The second phase of inflammation is characterized by the influx into the tissue of cells of the adaptive immune system, including lymphocytes. The subsequent resolution phase, when apoptosis of the excess leukocytes and engulfment by tissue macrophages takes place, is also characterized by repair of tissue damage by stromal cells, such as fibroblasts.

In chronic inflammation, the resolution of inflammatory lesions is disordered, with the maintenance of inflammatory cells, fibroblast hyperplasia, and eventual tissue destruction. The mechanisms that lead to these events are complex, but include enhanced recruitment, survival and retention of cells and impaired emigration.

The source of fibroblasts responsible for repair of wound lesions or in other fibrotic responses is controversial. The conventional hypothesis suggests that local quiescent fibroblasts migrate into the affected area, produce extracellular matrix proteins, and promote wound contraction or fibrosis. An alternative hypothesis is that circulating fibroblast precursors (called fibrocytes) present within the blood migrate to the sites of injury or fibrosis, where they differentiate and mediate tissue repair and other fibrotic responses.

Fibrocytes are known to differentiate from a CD14+ peripheral blood monocyte precursor population. Fibrocytes express markers of both hematopoietic cells (CD45, MHC class II, CD34) and stromal cells (collagen types I and III and fibronectin). Mature fibrocytes rapidly enter sites of tissue injury where they secrete inflammatory cytokines. Fibrocytes are also capable of secreting extracellular matrix proteins, other cytokines and pro-angiogenic molecules, which may result in fibrosis.

Control of fibrocyte differentiation is likely to be important in the control of many diseases and processes. Fibrocytes are associated with a variety of processes and diseases including scleroderma, keloid scarring, rheumatoid arthritis, lupus, nephrogenic fibrosing dermopathy, and idiopathic pulmonary fibrosis. They play a role in the formation of fibrotic lesions after *Schistosoma japonicum* infection in mice and are also implicated in fibrosis associated with autoimmune diseases. Fibrocytes have also been implicated in pathogenic fibrosis, fibrosis associated with radiation damage, Lyme disease and pulmonary fibrosis. CD34+ fibrocytes have also been associated with stromal remodeling in pancreatitis and stromal fibrosis, whereas lack of such fibrocytes is associated with pancreatic tumors and adenocarcinomas. Fibrosis additionally occurs in asthma patients and possibly other pulmonary diseases such as chronic obstructive pulmonary disease when fibrocytes undergo further differentiation into myofibroblasts.

Fibrocytes may also play a role in a variety of conditions, likely even some in which fibrocyte formation is not currently known. Some additional conditions may include congestive heart failure, other post-ischemic conditions, post-surgical scarring including abdominal adhesions, corneal refraction surgery, and wide angle glaucoma trabeculectomy. Fibrocytes are also implicated in liver fibrosis and cirrhosis. See Tatiana Kisseleva et al, *Bone Marrow-Derived Fibrocytes Participate in Pathogenesis of Liver Fibrosis,* 45 Journal of Hepatology 429-438 (September 2006); see also F. P. Russo et al, *The Bone Marrow Functionality Contributes to Liver Fibrosis,* 130(6) Gastroenterology 1807-21 (May 2006). Fibrocytes are important in the formation of tumors, particularly stromal tissue in tumors. Recent evidence also suggests that fibrocytes may further differentiate into adipocytes and thus play a role in obesity.

Serum Amyloid P

SAP, a member of the pentraxin family of proteins that include C-reactive protein (CRP), is secreted by the liver and circulates in the blood as stable pentamers. The exact role of SAP is still unclear, although it appears to play a role in both the initiation and resolution phases of the immune response. SAP binds to sugar residues on the surface of bacteria leading to their opsonisation and engulfment. SAP also binds to free DNA and chromatin generated by apoptotic cells at the resolution of an immune response, thus preventing a secondary inflammatory response. Molecules bound by SAP are removed from extracellular areas due to the ability of SAP to bind to all three classical Fcγ receptors (FcγR), with a preference for FcγRI (CD64) and FcγRII (CD32). After receptor binding, SAP and any attached molecule are likely engulfed by the cell.

FcγR are necessary for the binding of IgG to a wide variety of hematopoietic cells. Peripheral blood monocytes express both CD64 and CD32 (a subpopulation of monocytes express CD16), whereas tissue macrophages express all three classical FcγR. Clustering of FcγR on monocytes by IgG, either bound to pathogens or as part of an immune complex, initiates a wide variety of biochemical events. The initial events following receptor aggregation include the activation of a series of src kinase proteins. In monocytes, these include lyn, hck and fgr, which phosphorylate tyrosine residues on the ITAM motif of the FcR-γ chain associated with FcγRI and FcγRIII, the ITAM motif within the cytoplasmic domain of FcγRIIa or the ITAM motif with the cytoplasmic domain of FcγRIIb. Phosphorylated ITAMs lead to the binding of a second set of src kinases, including syk. Syk has been shown to be vital for phagocytosis of IgG-coated particles. However, the wide distribution of syk in non-hematopoietic cells and the evidence that syk is involved in both integrin and G-protein coupled receptor signaling, indicates that this molecule has many functions.

Both SAP and CRP augment phagocytosis and bind to Fcγ receptors on a variety of cells. CRP binds with a high affinity to FcγRII (CD32), a lower affinity to FcγRI (CD64), but does not bind FcγRIII (CD16). SAP binds to all three classical Fcγ receptors, with a preference for FcγRI and FcγRII, particularly FCγRI. Although there are conflicting observations on the binding of CRP to FcγR, both SAP and CRP have been shown to bind to Fc receptors and initiate intracellular signaling events consistent with FcγR ligation.

In human blood serum, males normally have approximately 32 μg/ml+/−7 μg/ml of SAP, with a range of 12-50 μg/ml being normal. Human females generally have approximately 24 μg/ml+/−8 μg/ml of SAP in blood serum, with a range of 8-55 μg/ml being normal. In human cerebral spinal fluid there is normally approximately 12.8 ng/ml SAP in human males and approximately 8.5 ng/ml in females. Combining male and female data, the normal SAP level in human serum is 26 μg/ml+/−8 μg/ml with a range of 12-55 μg/ml being normal. (The above serum levels are expressed as mean+/−standard deviation.)

IL-12

IL-12 has been previously implicated in fibrosis and fibrosing diseases, but most studies have focused on the role of IL-12 in promoting the Th1 immune response or by triggering the production of interferon-γ. The direct effects of IL-12 on fibrocyte formation do not appear to have been previously recognized.

Laminin-1

Laminins are extracellular matrix proteins involved in movement of monocytes from the circulation into tissues. In order for leukocytes to enter tissues, they must cross through endothelial cells and the surrounding basement membrane of blood vessel wall. This process involves the tethering, rolling and stopping of the leukocytes on the endothelial cells. Following adhesion to the endothelial cells, leukocytes then cross between the endothelial cells, through the blood vessel wall and into the tissues. The process of extravasation of cells through blood vessel walls alters their phenotype and function.

These events are controlled by a series of cell surface adhesion receptors, including integrins. Integrins bind to a wide variety of ligands, including extracellular matrix proteins (ECM), such as fibronectin, vitronectin, collagen and laminin. Matrix proteins are present within the basement of the blood vessel wall, including laminins. Laminin are a large family of glycoproteins, with a heterotrimeric structure of α, β and γ chains. The use of different α, β and γ chains leads to the expression of at least 12 different laminin isoforms. Different laminins are expressed at different stages of development and at different sites within the body.

Scleroderma

Scleroderma is a non-inherited, noninfectious disease that has a range of symptoms. It involves the formation of scar tissue containing fibroblasts in the skin and internal organs. The origin of the fibroblasts is unknown. In mild or early cases of scleroderma, there is a hardening of the skin, fatigue, aches and sensitivity to cold. In more severe and later stages, there is high blood pressure, skin ulcers, difficulty moving joints, and death from lung scarring or kidney failure. Approximately 300,000 people in the U.S. have scleroderma. The disease has similarities to lupus and rheumatoid arthritis. There is no cure or significant treatment for scleroderma and even diagnosis is difficult because there is no clinical test.

Nephrogenic Fibrosing Dermopathy

Nephrogenic fibrosing dermopathy (NFD) is a newly recognized scleroderma-like fibrosing skin condition. It develops in patients with renal insufficiency. Yellow scleral plaques and circulating antiphospholipid antibodies have been proposed as markers of NFD. Dual immunohistochemical staining for CD34 and pro-collagen in the spindle cells of NFD suggest that the dermal cells of NFD may represent circulating fibrocytes recruited to the dermis. Therefore, inhibition of fibrocyte formation may alleviate symptoms of this disease.

Asthma

Asthma affects more than 100 million people worldwide, and its prevalence is increasing. Asthma appears to be caused by chronic airway inflammation. One of the most destructive aspects of asthma is remodeling of the airways in response to chronic inflammation. This remodeling involves thickening of the lamina reticularis (the subepithelial reticular basement membrane surrounding airways) due to fibrosis. The airway passages then become constricted due to the thickened airway walls.

The thickened lamina reticularis in asthma patients contains abnormally high levels of extracellular matrix proteins such as collagen I, collagen III, collagen V, fibronectin and tenascin. The source of these proteins appears to be a specialized type of fibroblast called myofibroblasts.

In asthma patients, CD34+/collagen I+ fibrocytes accumulate near the basement membrane of the bronchial mucosa within 4 hours of allergen exposure. 24 hours after allergen exposure, labeled monocytes/fibrocytes have been observed to express α-smooth muscle actin, a marker for myofibroblasts. These observations suggest that in asthma patients allergen exposure causes fibrocytes from the blood to enter the bronchial mucosa, differentiate into myofibroblasts, and then cause airway wall thickening and obstruct the airways. Further, there is a correlation between having a mutation in the regulatory regions of the genes encoding monocyte chemoattractant protein 1 or TGFβ-1 and the severity of asthma. This also suggests that recruitment of monocytes and appearance of myofibroblasts lead to complications of asthma.

Thickening of the lamina reticularis distinguishes asthma from chronic bronchitis or chronic obstructive pulmonary disease and is found even when asthma is controlled with conventional medications. An increased extent of airway wall thickening is associated with severe asthma. No medications or treatments have been found to reduce thickening of the lamina reticularis. However, it appears likely that reducing the number of myofibroblasts found in the airway walls may reduce thickening or help prevent further thickening.

Idiopathic Pulmonary Fibrosis

Idiopathic pulmonary fibrosis (IPF) is a unique type of chronic fibrosing lung disease of unknown etiology. The sequence of the pathogenic mechanisms is unknown, but the disease is characterized by epithelial injury and activation, the formation of distinctive subepithelial fibroblast/myofibroblast foci, and excessive extracellular matrix accumulation. These pathological processes usually lead to progressive and irreversible changes in the lung architecture, resulting in progressive respiratory insufficiency and an almost universally terminal outcome in a relatively short period of time. While research has largely focused on inflammatory mechanisms for initiating the fibrotic response, recent evidence strongly suggests that disruption of the alveolar epithelium is an underlying pathogenic event. Given the role played by fibrocytes in wound healing and their known role in airway wall thickening in asthma, it appears likely that overproduction of fibrocytes may be implicated in IPF.

SUMMARY

The present invention may include compositions and methods for suppressing fibrocytes. In the context of the present invention, the term "suppressing fibrocytes" refers to one or more of inhibiting the proliferation of fibrocytes, inhibiting the development of fibrocytes, including the development or differentiation of a cell into a fibrocyte, and promoting the development or differentiation of fibrocytes into non-fibrocytic cell types.

In selected embodiments, fibrocytes may be suppressed in a target location by providing SAP, IL-12, Laminin-1, IgG aggregates, cross-linked IgG, cofactors of any of the above, and any combination thereof. (Designations for "SAP", "IL-12", "Laminin-1" and "IgG" as used herein also refer to functional fragments of these proteins unless it is clear that such fragments are excluded from the usage in a given context.) The target location may be located in vitro or in vivo. Specifically, the target location may be located in a mammal, such as a human patient.

In vivo the target location may include an entire organism or a portion thereof and the composition may be administered systemically or it may be confined to a particular area, such as an organ or tissue.

The compositions may include those supplied directly or produced in target location or the same organism as the target location, for instance through expression of a transgene. These compositions may be given in amount sufficient to increase concentrations above normal levels or to bring their concentrations up to normal levels or restore their normal activity levels. Concentrations or activity of certain of these compositions may be increased by stimulating natural production or suppressing normal degradation.

Suppressing fibrocytes may alleviate symptoms of numerous fibrosing diseases or other disorders caused by fibrosis. In a specific embodiment, administration of SAP, IL-12, Laminin-1, IgG aggregates, cross-linked IgG, cofactors of any of the above, and/or any combination thereof may be used to treat the effects of unwanted fibrocytes. For example, it may be used to treat fibrosis in the liver, kidney, lung, heart and pericardium, eye, skin, mouth, pancreas, gastrointestinal tract, brain, breast, bone marrow, bone, genitourinary, a tumor, or a wound.

Embodiments of the present invention also include assays to detect the ability of a sample to suppress fibrocytes. In one embodiment, normal cells (e.g., cells capable of differentiating into fibrocytes, like monocytes for example) may be supplied with the sample. The sample may include normal SAP. It may also include SAP or a biological fluid from a patient such as a patient with a fibrosing disease, or it may include a potential drug. In another embodiment, the sample may include normal SAP while the cells may be derived from a patient and may be abnormal or suspected of being abnormal. In either type of assay, the effects on fibrocyte suppression may be compared with a normal control to detect any increases or decreases in differentiation as compared to normal. This may indicate the presence or absence of a fibrosing disease.

BRIEF DESCRIPTION OF THE DRAWINGS

The following figures form part of the present specification and are included to further demonstrate certain aspects of the present invention. The invention may be better understood by reference to one or more of these drawings in combination with the detailed description presented herein.

FIG. 1 illustrates the effects of serum and plasma on the rapid differentiation of fibroblast-like cells.

In FIG. 1A peripheral blood mononuclear cells (PBMC) at $2.5 \times 10^5$ per ml were cultured in serum-free medium for 3 or 6 days in the presence or absence of 0.1% human serum and then examined by microscopy for the appearance of fibroblast-like cells. Bar is 100 µm.

In FIG. 3A fractions were analyzed by PAGE on a 4-20% reducing gel and stained with coomassie blue. M indicates molecular weight markers. Lane 1 contained plasma, lane 2 contained $BaCl_2$ supernatant, lane 3 contained wash 1, lane 4 contained wash 2, lane 5 contained $BaCl_2$ precipitate, lane 6 contained $BaCl_2$ precipitate, lane 7 contained heparin flow through, lane 8 contained the heparin fraction, lane 9 contained High Q flow through, lane contained the 10 High Q fraction, lane 11 contained the gel purified fraction. Lanes 1-5 were diluted 1:500 in sodium phosphate buffer, lanes 6-11 were undiluted.

Active fractions eluted off the High Q ion exchange column and gel slices were analyzed by 4-20% PAGE on a native gel in FIG. 3B and a reducing gel in FIG. 3C. NM indicates native gel markers, RM indicates reduced gel markers. In FIG. 3C lanes 1-3 are control gel samples, lane 4 contained active fraction. In FIG. 3D fractions were assessed by western blotting, using a rabbit anti-SAP antibody. Lanes 1-11 correspond to those in FIG. 3A.

FIG. 5 shows the effect of depletion of SAP from plasma in a fibrocyte differentiation assay.

FIG. 6 shows the effects of various cytokines on monocyte differentiation into fibrocytes.

FIG. 9 shows the effects of ligation and cross-linking of Fc receptors on monocyte to fibrocyte differentiation. Soluble immune complexes (ovalbumin-antibody), particulate immune complexes, including opsonised sheep red blood cells (SRBC) and heat-aggregated IgG were used.

FIG. 12 shows cross sections of rat lungs after administration of saline or bleomycin with or without SAP.

DETAILED DESCRIPTION

Fibrocyte Suppression

Figure 1B:
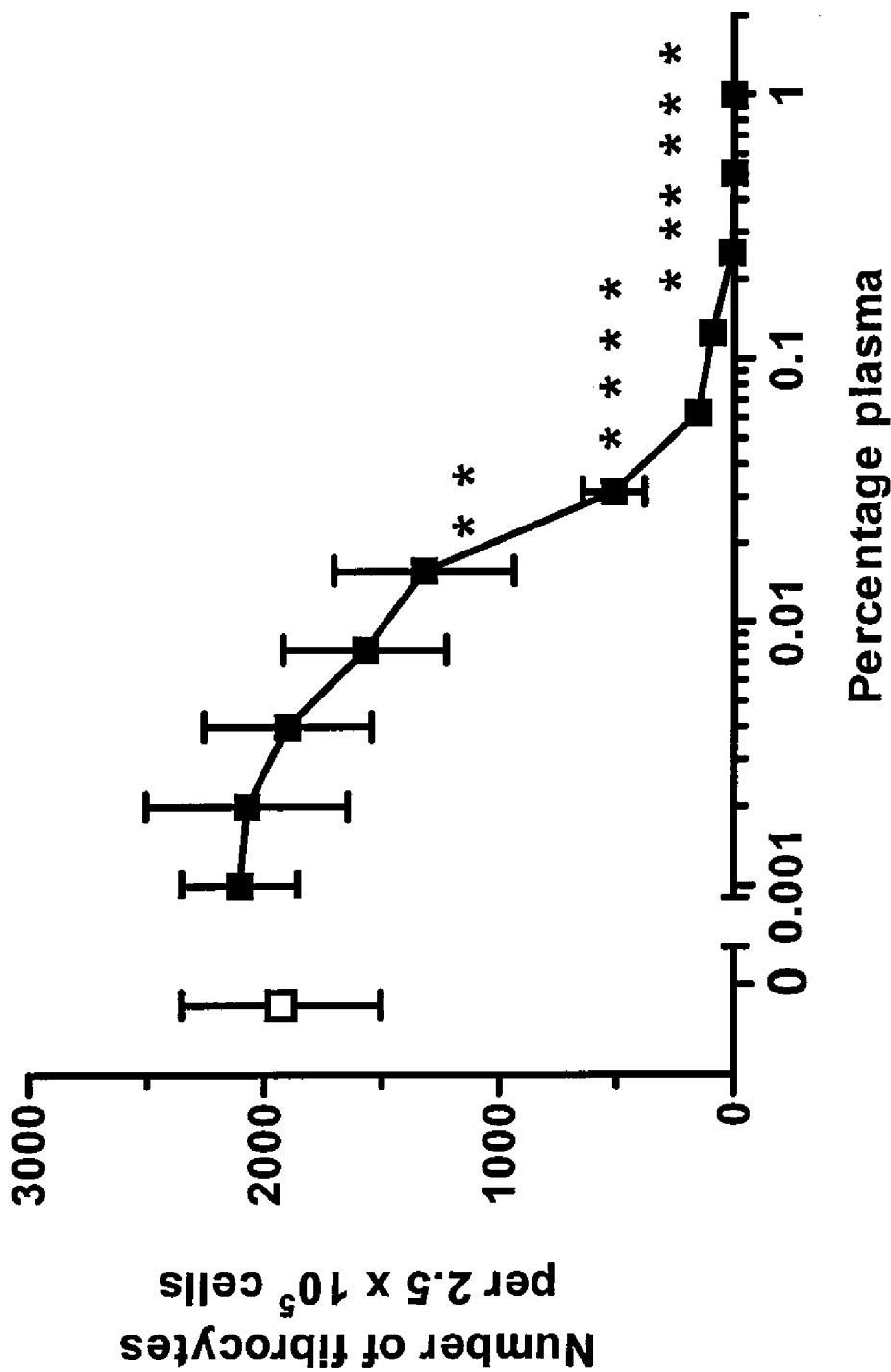
In FIG. 1B PBMC at $2.5 \times 10^5$ per ml were cultured in serum-free medium for 6 days in dilutions of human plasma. Cells were then air-dried, fixed, stained, and fibrocytes were enumerated by morphology. Results are expressed as mean±SD of the number of fibrocytes per $2.5 \times 10^5$ PBMCs (n=5 experiments). Stars indicate statistically significant differences from samples without plasms.

The regulation of events leading to fibrosis involves the proliferation and differentiation of fibrocytes. Fibrocytes are a distinct population of fibroblast-like cells derived from peripheral blood monocytes that normally enter sites of tissue injury to promote angiogenesis and wound healing. Culturing CD14+ peripheral blood monocytes in the absence of serum or plasma leads to the rapid differentiation of fibrocytes. This process occurs within 72 hours and is suppressed by the presence of serum or plasma. The factor in serum that suppresses the rapid appearance of fibrocytes is serum amyloid P (SAP). Further, a cohort of patients with the fibrosing disease scleroderma have sera with a poor ability to suppress fibrocyte differentiation and exhibit a correspondingly low level of SAP. These results suggest that low levels of SAP in the circulation or the peripheral tissues lead to or play a part in pathological processes such as fibrosis. Monocyte differentiation assays have also revealed that IL-12, Laminin-1 and conjugated IgG molecules also suppress differentiation of monocytes into fibrocytes.

Compositions containing one or more of the fibrocyte formation suppressors may be used to suppress fibrosis in inappropriate locations and in fibrosing disorders and chronic inflammatory conditions, inter alia.

Compositions may be applied locally or systemically. In specific embodiments, compositions containing SAP may be operable to raise SAP concentration in target locations to approximately at least 0.5 µg/ml. In humans, $I^{125}$ radiolabelled SAP has been previously administered to study patients with amyloidosis. In the treatments, approximately 100 µg of SAP was administered to an adult human. Accordingly, administration of approximately 100 µg of SAP systemically to an adult human is safe. Higher dosages may also be safe under appropriate conditions.

SAP supplied in certain compositions of the present invention may include the entire SAP protein or a portion thereof, preferably the portion functional in suppression fibrocyte formation. In an exemplary embodiment, the functional portion of SAP is selected from the region that does not share sequence homology with CRP, which has no effect on fibrocyte formation. For instance amino acids 65-89 KERVGEY- SLYIGRHKVTSKVIEKFP (SEQ ID NO:1) of SAP are not homologous to CRP. Amino acids 170-181 ILSAYQGT-PLPA (SEQ ID NO:2) and 192-205 IRGYVIIKPLV (SEQ ID NO:3) are also not homologous. Additionally a number of single amino acid differences between the two proteins are known and may result in functional differences.

Compositions containing IL-12 may be operable to raise the IL-12 concentration in target locations to approximately 0.1 to 10 ng/ml. Compositions containing Laminin-1 may be operable to raise the laminin-1 concentration in target locations to approximately 1 to 10 μg/ml. Compositions containing aggregated IgG may be operable to raise aggregate IgG concentrations in target locations to approximately 100 μg/ml. The compositions may also be supplied in combinations or with cofactors. Compositions may be administered in an amount sufficient to restore normal levels, if the composition is normally present in the target location, or they may be administered in an amount to raise levels above normal levels in the target location.

The above compositions may be supplied to a target location from an exogenous source, or they may be made in vivo by cells in the target location or cells in the same organism as the target location. These compositions may be isolated from donated human tissues, including biological fluids. They may be also be made as a recombinant protein in bacteria, tissue culture cells, or any other type of cells or tissues known to the art, or in whole animals. They may also be made synthetically or by any other methodology known to the art. If these compositions are made in vivo, they may be the expression product of a transgene or they may result from enhancement of production in an existing in vivo source. Levels of these compositions, if they are normally present in a target location, may also be raised by reducing their normal rates of degradation. Additionally, it may be possible to increase the fibrocyte suppression ability of these compositions, for instance by supplying cofactors.

In a specific embodiment, the compositions may include SAP coupled to an agent to prolong its serum half-life or otherwise to facilitate delivery of the SAP to the area of the fibrosing disease, as opposed to removal by the body as waste. For example, the SAP may be conjugate to a biocompatible polymer such as PEG, a poly(amino acid), or a polysaccharide.

Compositions of the present invention may be in any physiologically appropriate formulation. They may be administered to an organism topically, by injection, by inhalation, orally or by any other effective means.

Disease Targets

The same compositions and methodologies described above to suppress fibrocytes may also be used to treat or prevent conditions resulting from inappropriate fibrocyte proliferation or differentiation. For example, they may treat or prevent a condition occurring in the liver, kidney, lung, heart and pericardium, eye, skin, mouth, pancreas, gastrointestinal tract, brain, breast, bone marrow, bone, genitourinary, a tumor, or a wound.

Generally, they may treat or prevent fibrosis resulting from conditions including but not limited to rheumatoid arthritis, lupus, pathogenic fibrosis, fibrosing disease, fibrotic lesions such as those formed after *Schistosoma japonicum* infection, radiation damage, autoimmune diseases, Lyme disease, chemotherapy induced fibrosis, HIV or infection-induced focal sclerosis, failed back syndrome due to spinal surgery scarring, abdominal adhesion post surgery scarring, fibrocystic formations, fibrosis after spinal injury, surgery-induced fibrosis, mucosal fibrosis, peritoneal fibrosis caused by dialysis, and Adalimumab-associated pulmonary fibrosis.

Specifically, in the liver, they may treat or prevent fibrosis resulting from conditions including but not limited to alcohol, drug, and/or chemically induced cirrhosis, ischemia-reperfusion injury after hepatic transplant, necrotizing hepatitis, hepatitis B, hepatitis C, primary biliary cirrhosis, and primary sclerosing cholangitis.

Relating to the kidney, they may treat or prevent fibrosis resulting from conditions including but not limited to proliferative and sclerosing glomerulonephritis, nephrogenic fibrosing dermopathy, diabetic nephropathy, renal tubulointerstitial fibrosis, and focal segmental glomerulosclerosis.

Relating to the lung, they may treat or prevent fibrosis resulting from conditions including but not limited to pulmonary interstitial fibrosis, sarcoidosis, pulmonary fibrosis, idiopathic pulmonary fibrosis, asthma, chronic obstructive pulmonary disease, diffuse alveolar damage disease, pulmonary hypertension, neonatal bronchopulmonary dysplasia, chronic asthma, and emphysema. There are several subnames or synonyms for pulmonary fibrosis including, but not limited to, cryptogenic fibrosing alveolitis, diffuse interstitial fibrosis, idiopathic interstitial pneumonitis, Hamman-Rich syndrome, silicosis, asbestosis, berylliosis, coal worker's pneumoconiosis, black lung disease, coal miner's disease, miner's asthma, anthracosis, and anthracosilicosis.

Relating to the heart and/or pericardium, they may treat or prevent fibrosis resulting from conditions including but not limited to myocardial fibrosis, atherosclerosis, coronary artery restenosis, congestive cardiomyopathy, heart failure, and other post-ischemic conditions.

Relating to the eye, they may treat or prevent fibrosis resulting from conditions including but not limited to exophthalmos of Grave's disease, proliferative vitreoretinopathy, anterior capsule cataract, corneal fibrosis, corneal scarring due to surgery, trabeculectomy-induced fibrosis, progressive subretinal fibrosis, multifocal granulomatous chorioretinitis, and other eye fibrosis.

Relating to the skin, they may treat or prevent fibrosis resulting from conditions including but not limited to Depuytren's contracture, scleroderma, keloid scarring, psoriasis, hypertrophic scarring due to burns, atherosclerosis, restenosis, and psuedoscleroderma caused by spinal cord injury.

Relating to the mouth and/or esophagus, they may treat or prevent fibrosis resulting from conditions including but not limited to periodontal disease scarring, gingival hypertrophy secondary to drugs, and congenital esophageal stenosis.

Relating to the pancreas, they may treat or prevent fibrosis resulting from conditions including but not limited to pancreatic fibrosis, stromal remodeling pancreatitis, and stromal fibrosis.

Relating to the gastrointestinal tract, they may treat or prevent fibrosis resulting from conditions including but not limited to collagenous colitis, villous atrophy, crypt hyperplasia, polyp formation, fibrosis of Crohn's disease, and healing gastric ulcer.

Relating to the brain, they may treat or prevent fibrosis resulting from conditions including but not limited to glial scar tissue.

Relating to the breast, they may treat or prevent fibrosis resulting from conditions including but not limited to fibrocystic disease and desmoplastic reaction to breast cancer.

Relating to the bone marrow, they may treat or prevent fibrosis resulting from conditions including but not limited to fibrosis in myelodysplasia and neoplastic diseases.

Relating to the bone, they may treat or prevent fibrosis resulting from conditions including but not limited to rheumatoid pannus formation.

Relating to the genitourinary system, they may treat or prevent fibrosis resulting from conditions including but not limited to endometriosis, uterine fibroids, ovarian fibroids, and Peyronie's disease.

Relating to radiation induced damage, they may treat or prevent fibrosis related to, but not limited to, treatment of head and neck cancer, ovarian cancer, prostate cancer, lung cancer, gastrointestinal cancer, colon cancer, and breast cancer.

The invention also includes a method of suppressing fibrocytes or treating or preventing a fibrosing disease or asthma by activating any component of the Fc signaling pathway in cells normally activated by SAP. This pathway is described in detail in Daeron, Marc, "Fc Receptor Biology", Annu. Rev. Immunology 15:203-34 (1997). In an exemplary embodiment, a portion of the pathway that is not shared with other signaling cascades or only a limited number of non-critical signaling cascades is selected for activation to minimize side-effects.

In a particular embodiment, pulmonary fibrosis or other pulmonary fibrosing diseases may be treated by administration of SAP. Treatment may reduce cellular growth associated with fibrosis and also collagen deposition. Treatment may prevent further fibrosis or reduce the effects of current fibrosis. SAP may be administered in a dose of approximately 1.6 µg/g of bodyweight or in another dose able to approximately double the serum concentration of SAP in the patient. Administration may be intravenous and may take place every other day for a selected duration. This dose, method of administration and administration schedule may also be useful in treating other fibrosing diseases.

Differentiation Assays

Another aspect of the invention relates to assays to detect the ability of a sample to suppress fibrocytes. In serum-free medium, normal monocytes form fibrocytes in two to three days. Normal serum, blood or other biological fluids suppress the formation of fibrocytes from normal monocytes over a specific dilution range. Thus the assay may be used to test whether a sample can modulate differentiation of monocytes into fibrocytes in serum-free medium. It may also be used to determine whether sample monocytes differentiate normally into fibrocytes in serum-free medium and if they respond normally to serum, SAP or other factors affecting this differentiation.

In a specific embodiment, the assay may be used to determine whether a patient's biological fluid has a decreased or increased ability to suppress fibrocytes. If suppression by SAP is to be tested, any biological fluid in which SAP is normally or transiently present may be used in the present invention, including whole blood, serum, plasma, synovial fluid, cerebral spinal fluid and bronchial fluid. A decreased ability of any of these fluids to suppress fibrocytes may be indicative of a fibrosing disease or the propensity to develop such a disease.

Although in many patients a decreased ability of a biological fluid to suppress fibrocyte formation may be due to low levels of SAP, this is not necessarily the case. SAP may be present at normal levels, but exhibit decreased suppressive activity due to defects in the SAP itself or the absence or presence of a cofactor or other molecule. Methods of determining the more precise nature of the suppression problem, such as use of ELISAs, electrophoresis, and fractionation will be apparent to one skilled in the art.

The methodology described above may also be used to determine whether certain potential drugs that affect fibrocyte proliferation or differentiation may or may not be appropriate for a patient.

In another specific embodiment, the assay may be used to determine if a patient's cells are able to differentiate into fibrocytes in serum-free medium and if they respond normally to a biological fluid, SAP or another composition. More particularly, if a patient with a fibrosing disease appears to have normal levels of SAP, particularly functional SAP, it may be advisable to obtain a sample of the patient's cells (e.g., monocytes) to determine if they are able to readily differentiate into fibrocytes even in the presence of serum or SAP. If the patient's cells are able to differentiate in the presence of normal SAP, then the cells themselves and not any SAP deficiencies may be the cause of the patient's disease.

This assay may also be used to determine if any drugs are appropriate for a particular patient.

Finally, in another specific example, the assay may be used to test the effects of a drug or other composition on a cell's differentiation into fibrocytes. The assay may be used in this manner to identify potential drugs designed to modulate fibrocyte formation, or it may be used to screen for any potential adverse effects of drugs intended for other uses.

The following examples are included to demonstrate specific embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1

Inhibition of Fibrocyte Formation

While examining the possible role of cell density in the survival of peripheral blood T cells, it was observed that in serum-free medium PBMC gave rise to a population of fibroblast-like cells. These cells were adherent and had a spindle-shaped morphology (FIG. 1A). Approximately 0.5-1% of PBMC differentiated into fibroblast-like cells in serum-free medium, and this occurred in tissue culture treated plasticware and borosilicate and standard glass slides.

The rapid appearance of these cells, within 3 days of culture, was inhibited by human serum or plasma. To examine this process in more detail, PBMC were cultured at $5 \times 10^5$ cells per ml in serum-free medium containing increasing concentrations of human plasma for 6 days. When plasma was present at concentrations between 10% and 0.5%, the fibroblast-like cells did not differentiate (FIG. 1B). However, at or below 0.1% serum, fibroblast-like cells rapidly developed. The activity in the serum that inhibited fibrocyte formation was retained by a 30 kDa cutoff spin-filter (data not shown). If serum was heated to 56° C. for 30 minutes, the efficacy was reduced 10 fold, and heating to 95° C. abolished the inhibitory activity (data not shown).

These data suggest that the inhibitory factor is a protein. As the inhibitory factor was present in human serum, it indicated that the activity was unlikely to be involved with the coagulation system. The inhibitory factor also appeared to be an evolutionary conserved protein as bovine, equine, caprine, and rat sera were also able to inhibit the appearance of these fibroblast-like cells (data not shown).

Example 2

Characterization of Fibroblast-Like Cells

The differentiation of these fibroblast-like cells from peripheral blood suggested that they might be peripheral blood fibrocytes. Fibrocytes are a population derived from peripheral blood monocytes that differentiate in vitro and in vivo into fibroblast-like cells. They rapidly enter wound sites and are capable of presenting antigens to T cells. Their phenotype is composed of both hematopoietic markers, such as CD45 and MHC class II, and stromal markers, such as collagen I and fibronectin. However in order to identify these cells, PBMC were generally cultured for 1-2 weeks in medium containing serum.

To characterize whether the cells observed in the system were fibrocytes, PBMC were depleted of T cells with anti-CD3, B cells with anti-CD19, monocytes with anti-CD14 or all antigen presenting cells with anti-HLA class II and then cultured in serum-free conditions for 6 days. Depletion of PBMC with anti-CD3 or anti-CD19 did not deplete fibroblast-like cells from PBMC when cultured in serum-free cultures (data not shown). Depletion of antigen presenting cells with anti-HLA class II or monocytes with anti-CD14 antibody did prevent the appearance of fibroblast-like cells, indicating that the fibroblast-like cells are derived from monocytes and not a dendritic cell population.

Figure 2:
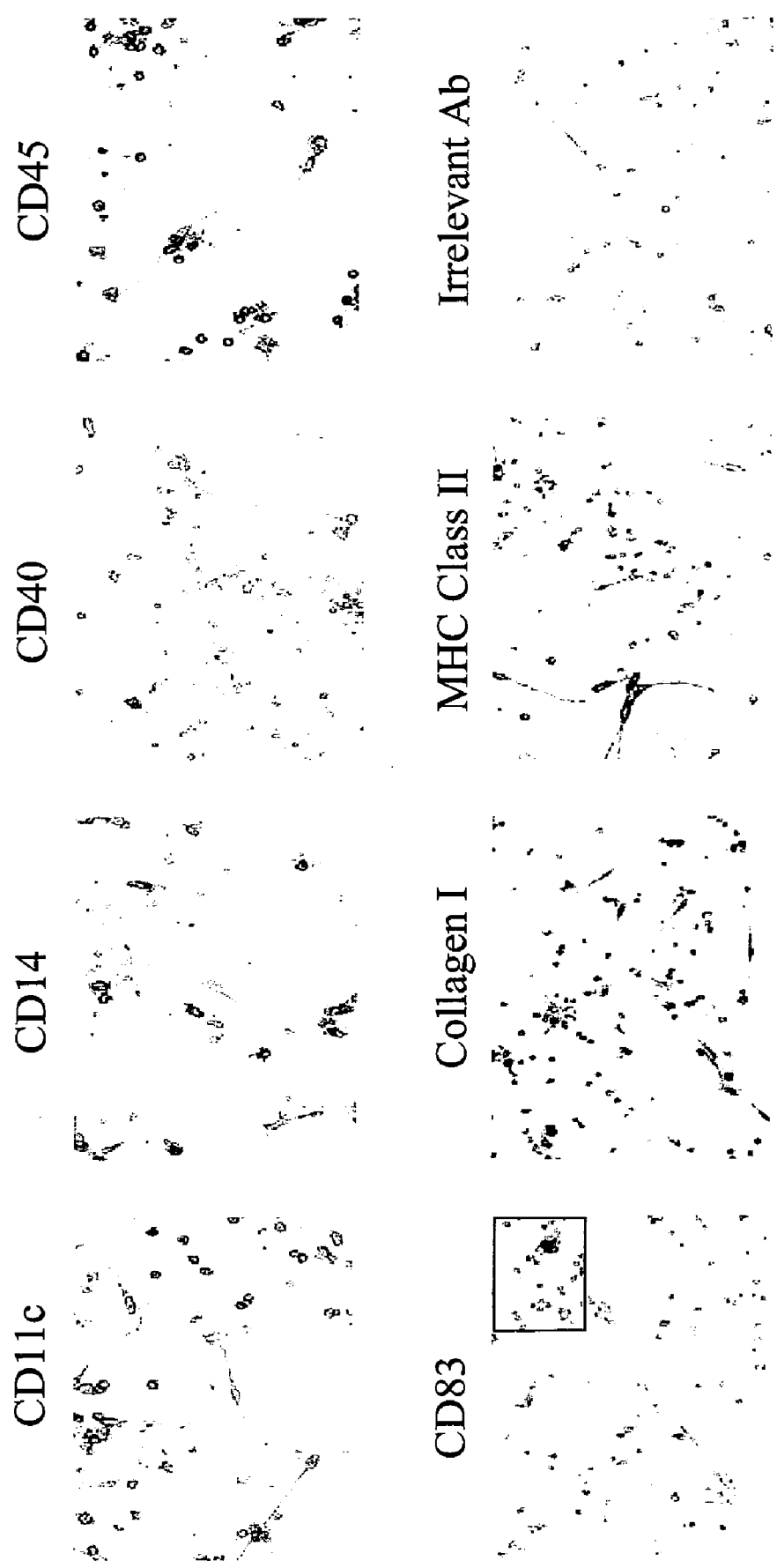
FIG. 2 illustrates the expression of surface molecules on fibroblast-like cells. PBMC were cultured on glass slides in serum-free medium for 6 days. Cells were air-dried and analyzed by immunohistochemistry. Monoclonal antibodies used are as indicated, and identified by biotin-conjugated goat anti-mouse Ig followed by ExtrAvidin peroxidase. Cells were counterstained with Mayer's haematoxylin to identify nuclei. Positive staining was identified by brown staining, nuclei are counterstained blue. An insert for CD83 was used to indicate positive staining on a dendritic cell.

To further characterize the fibroblast-like cells, PBMC were cultured in serum-free medium for 5 days on glass slides. Cells were then air-dried, fixed in acetone and labeled with a variety of antibodies (Table 1 and FIG. 2). Fibrocytes express CD11a, CD11b, CD45, CD80, CD86, MHC class II, collagen I, fibronectin, the chemokine receptors CCR3, CCR5, CCR7, CXCR4 and α-smooth muscle actin. In the above culture conditions, the fibroblast-like cells in the present experiment also expressed all these markers. Fibrocytes are negative for CD1a, CD3, CD19, CD38 and vWF, as were the fibroblast-like cells in the present experiment. Based on these data it appears that the fibroblast-like cells observed in the experiments were fibrocytes. Further experiments were conducted to extend this phenotype. In the above conditions, the fibrocytes expressed several β1 integrins including α1 (CD49a), α2 (CD49b), α5 (CD49e), β1 (CD29) and β3 (CD61) along with high levels of β2 (CD18), but were negative for α3, α4, α6 α4β7, αE and CLA (FIG. 2 and Table 1).

TABLE 1

Expression of surface markers on Fibrocytes

| Marker | Alternative Name | Fibrocyte Expression |
| --- | --- | --- |
| CD11a | LFA-1 | positive |
| CD11b | Mac-1 | positive |
| CD11c |  | positive |
| CD13 |  | positive |
| CD18 | β2 integrin | positive |
| CD29 | β1 integrin | positive |
| CD34 |  | positive |
| CD40 |  | weak positive |
| CD45 | LCA | positive |
| CD49a | α1 integrin | weak positive |
| CD49b | α2 integrin | negative |
| CD49e | α5 integrin | positive |
| CD51 |  | positive |
| CD54 | ICAM-1 | positive |
| CD58 | LFA-3 | positive |
| CD61 | β3 integrin | positive |
| CD80 | B7-1 | weak positive |
| CD86 | B7-2 | positive |
| CD105 | Endoglin | positive |
| CD148 |  | positive |
| MHC class II |  | positive |
| CD162 | PSGL-1 | positive |
| CCR1 |  | weak positive |
| CCR3 |  | weak positive |
| CCR4 |  | weak positive |
| CCR5 |  | weak positive |
| CCR7 |  | weak positive |
| CCR9 |  | weak positive |
| CXCR1 |  | positive |
| CXCR3 |  | positive |
| CXCR4 |  | weak positive |
| Collagen I |  | positive |
| Collagen III |  | positive |
| Fibronectin |  | positive |
| α Smooth Muscle Actin |  | positive |
| Vimentin |  | positive |
| CD1a |  | negative |
| CD3 |  | negative |
| CD10 |  | negative |
| CD14 |  | negative |
| CD19 |  | negative |
| CD25 |  | negative |
| CD27 |  | negative |
| CD28 |  | negative |
| CD38 |  | negative |
| CD49c | α3 integrin | negative |
| CD49d | α4 integrin | negative |
| CD49f | α6 integrin | negative |
| CD69 |  | negative |
| CD70 | CD27-L | negative |
| CD90 |  | negative |
| CD103 | αE integrin | negative |
| CD109 |  | negative |
| CD154 | CD40-L | negative |
| α4β7 |  | negative |
| CLA |  | negative |
| CCR2 |  | negative |
| CCR6 |  | negative |
| CXCR2 |  | negative |
| CXCR5 |  | negative |
| CXCR6 |  | negative |
| Cytokeratin |  | negative |
| vWF |  | negative |

To obtain the data in Table 1, PBMC were cultured in the wells of 8 well glass slides at $2.5 \times 10^5$ cells per ml (400 µl per well) in serum-free medium for 6 days. Cells were then air dried, fixed in acetone and stained by immunoperoxidase. Cells were scored positive or negative for the indicated antigens, compared to isotype-matched control antibodies.

Example 3

Characterization of the Fibrocyte Inhibitory Factor

The initial characterization of the serum factor that prevents rapid fibrocyte differentiation indicated that the factor was a heparin-binding molecule that eluted off an ion exchange column (High Q) as one of four proteins. By sequencing tryptic fragments of protein in a band cut from a native gel, one of these proteins was identified as C4b-binding protein (C4BP). C4b-binding protein is a 570 kDa protein, composed of seven alpha chains (70 kDa) and usually a single beta chain (40 kDa), which is involved in regulating the decay of C4b and C2a components of the complement system. C4BP also interacts with the vitamin K-dependent anticoagulant protein S. The C4BP/Protein S complex can be purified from serum or plasma using $BaCl_2$ precipitation.

Figure 3:
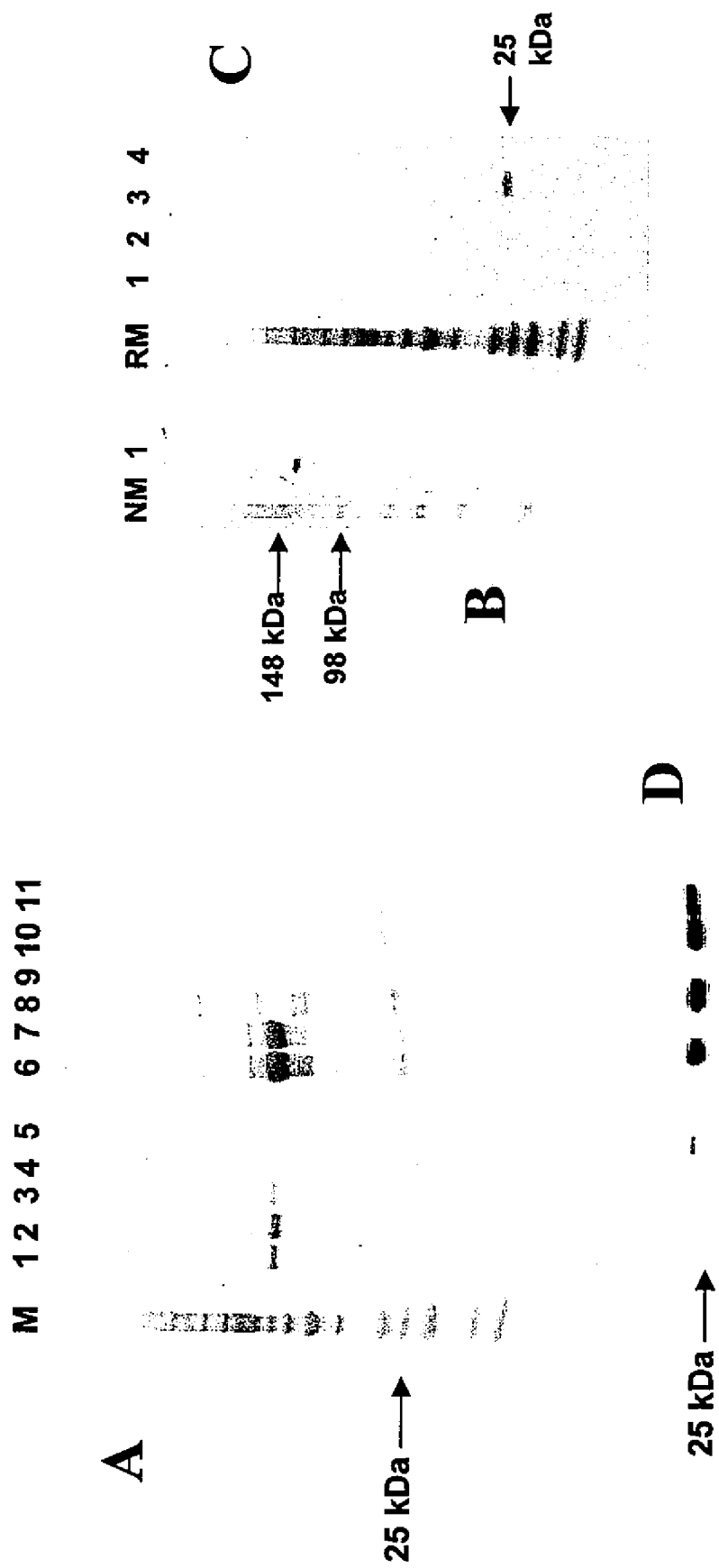
FIG. 3 illustrates the characterization of the molecule present in plasma that inhibits fibrocyte differentiation. Citrated plasma was treated with $BaCl_2$ and the precipitated material was collected by centrifugation and dialyzed against 10 mM sodium phosphate containing 10 mM EDTA and protease inhibitors. This material was then fractionated by heparin and ion exchange chromatography.

To assess whether C4BP, or an associated protein, was the factor responsible for inhibiting fibrocyte differentiation, citrated plasma was treated with $BaCl_2$. The inhibitory factor was present in the $BaCl_2$ precipitate (FIG. 3 and Table 2). This fraction was applied to a heparin column and the fractions, eluted by increasing concentrations of NaCl, were assessed for their ability to inhibit monocyte to fibrocyte differentiation in serum free medium. The active factor was eluted off the heparin column in a peak at 200 mM NaCl (FIG. 3 and Table 2). A slight increase in the yield suggested that this step may have removed a factor that slightly interfered with the activity of the factor.

The fractions from the 200 mM peak were pooled and further fractionated by High Q ion exchange chromatography. A small peak eluting at 300 mM NaCl contained activity that inhibited fibrocyte differentiation. Analysis of the proteins present in this fraction indicated that the major band was a 27 kDa protein. Although the ion exchange chromatography led to a reduction in the amount of SAP recovered (FIG. 3A, lanes 8-10 and FIG. 3D, lane 8-10) this step did remove several contaminating proteins. After the ion exchange step the only discernable contaminant was albumin at 65 kDa (FIG. 3A, lane 10).

The high Q fraction was concentrated and fractionated by electrophoresis on a non-denaturing polyacrylamide gel, followed by elution of the material in gel slices. A single band that migrated at approximately 140 kDa was able to inhibit differentiation (FIG. 3B). This band had a molecular weight of 27 kDa on a reducing polyacrylamide gel, suggesting that the native conformation of the protein was a pentamer (FIG. 3C). This band was excised from the gel, digested with trypsin and analyzed by MALDI mass spectrometry. Three major and two minor peptides were identified: VFVFPR (SEQ ID NO:4), VGEYSLYIGR (SEQ ID NO:5), AYSLFSYNTQGR (SEQ ID NO:6), QGYFVEAQPK (SEQ ID NO:7) and IVLGQEQDSYGGK (SEQ ID NO:8). These sequences exactly matched amino acid sequences 8-13, 68-77, 46-57, 121-130 and 131-143 of serum amyloid P.

To confirm that the active fractions contained SAP, fractions collected from column chromatography were analyzed by western blotting (FIG. 3D). The presence of SAP at 27 kDa was detected in all fractions that inhibited fibrocyte differentiation (FIG. 3D, lanes 6, 8, 10 and 11). A considerable amount of SAP was present in the supernatant from the $BaCl_2$ precipitation step indicating that this procedure was inefficient, with the recovery of only approximately 10-15% of the fibrocyte inhibitory activity in the $BaCl_2$ pellet (FIG. 3A, lane 2). In order to remove the known problem of anti-SAP antibodies binding to immunoglobulins when used with western blotting, the antibody was pre-incubated with human IgG bound to agarose. Fractions were also analyzed for the presence of CRP, C4BP and protein S. Western blotting indicated that C4BP and Protein S were present in plasma, and in the barium precipitation, but were absent from the active fractions collected from heparin chromatography (data not shown).

TABLE 2

Recovery of protein and fibrocyte inhibitory activity from fractionated human plasma

|  | Volume (ml) | Protein (mg/ml) | Total protein (mg) | Yield (%) |
|---|---|---|---|---|
| Plasma | 250 | 70 | 17,500 | 100 |
| $BaCl_2$ supernatant | 240 | 60 | 14,400 | 82.3 |
| $BaCl_2$ precipitate | 31 | 1 | 31 | 0.18 |
| Heparin fraction | 4.3 | 0.25 | 1.075 | 0.006 |
| High Q fraction | 1.96 | 0.05 | 0.098 | 0.00056 |
| Gel slice | 0.075 | 0.025 | 0.0018 | 0.00001 |

|  | Activity (U/ml) | Total activity (U) | Yield (%) | Specific activity (U/mg) |
|---|---|---|---|---|
| Plasma | 10,000 | $2.5 \times 10^6$ | 100 | 143 |
| $BaCl_2$ supernatant | 6,666 | $1.6 \times 10^6$ | 64 | 111 |
| $BaCl_2$ precipitate | 1,666 | $5.1 \times 10^4$ | 2 | 1,645 |
| Heparin fraction | 500 | 2,150 | 0.086 | 2000 |
| High Q fraction | 400 | 720 | 0.029 | 7,300 |
| Gel slice | 2000 | 150 | 0.006 | 80,000 |

Plasma was fractionated by $BaCl_2$ precipitation, heparin and ion exchange chromatography. Protein concentrations were assessed by spectrophotometry at 280 nm. Inhibition of fibrocyte differentiation was assessed by morphology. The fibrocyte inhibitory activity of a sample was defined as the reciprocal of the dilution at which it inhibited fibrocyte differentiation by 50%, when added to serum-free medium.

SAP may also be detected by ELISA using the following methodology:

Maxisorb 96 well plates (Nalge Nunc International, Rochester, N.Y.) were coated overnight at 4° C. with monoclonal anti-SAP antibody (SAP-5, Sigma) in 50 mM sodium carbonate buffer pH 9.5. Plates were then incubated in Tris buffered saline pH 7.4 (TBS) containing 4% BSA (TBS-4% BSA) to inhibit non-specific binding. Serum and purified proteins were diluted to 1/1000 in TBS-4% BSA, to prevent SAP from aggregating and incubated for 60 minutes at 37° C. Plates were then washed in TBS containing 0.05% Tween-20. Polyclonal rabbit anti-SAP antibody (BioGenesis) diluted 1/5000 in TBS-4% BSA was used as the detecting antibody. After washing, 100 pg/ml biotinylated goat $F(ab)_2$ anti-rabbit (Southern Biotechnology Inc.) diluted in TBS-4% BSA was added for 60 minutes. Biotinylated antibodies were detected by ExtrAvidin peroxidase (Sigma). Undiluted peroxidase substrate 3,3,5,5-tetramethylbenzidine (TMB, Sigma) was incubated for 5 minutes at room temperature before the reaction was stopped by 1N HCl and read at 450 nm (BioTek Instruments, Winooska, Vt.). The assay was sensitive to 200 pg/ml.

Example 4

Specificity of Serum Amyloid P

Figure 4:
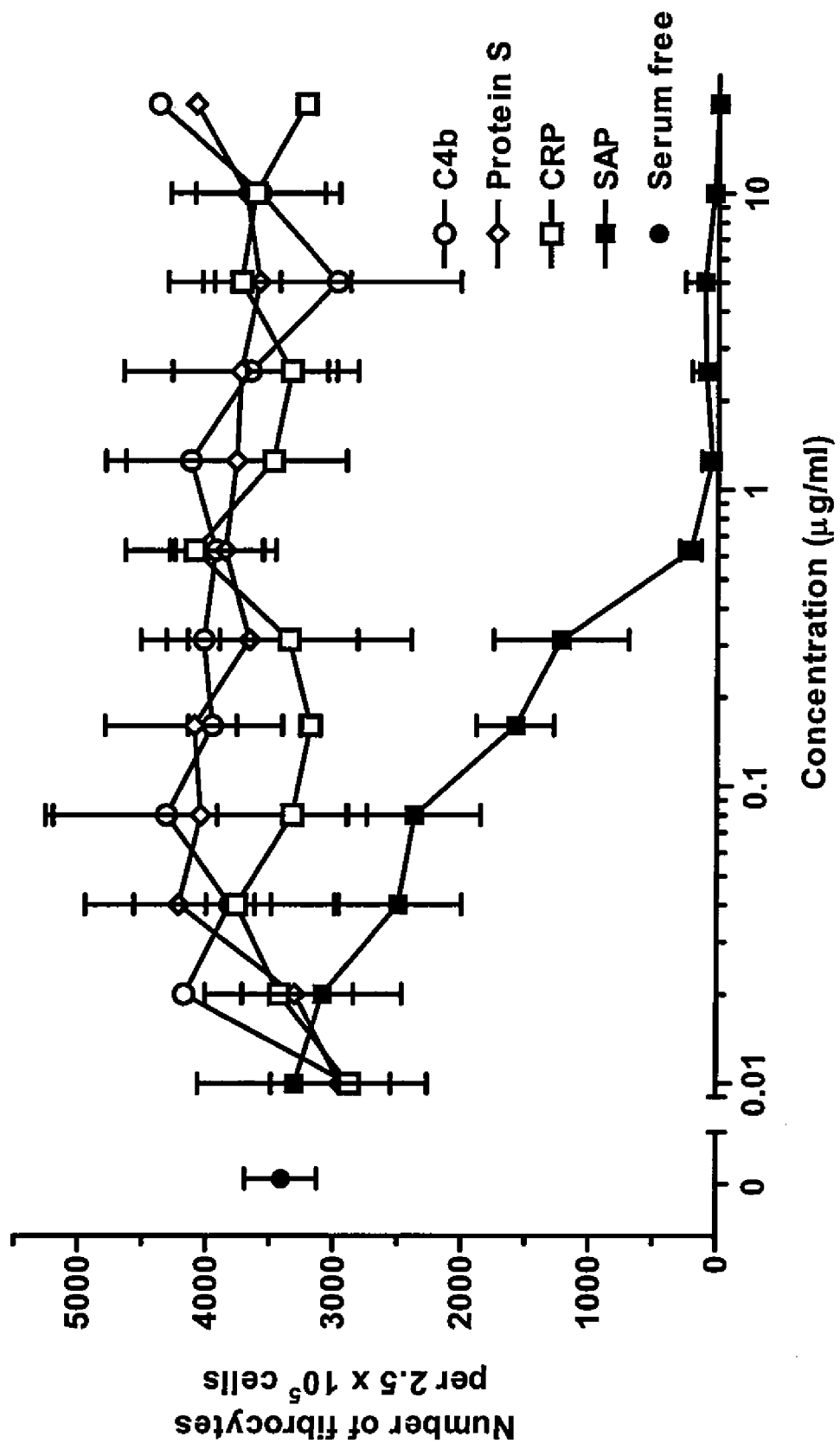
FIG. 4 shows the inhibition of fibrocyte formation by SAP, but not CRP or other plasma proteins. PBMC at $2.5 \times 10^5$ per ml were cultured in serum-free medium for 6 days in the presence of commercially available purified SAP (filled square), CRP (open square), Protein S (open diamond) or C4b (open circle) and then examined for the appearance of fibroblast-like cells. Cells were then air-dried, fixed, stained and fibrocytes enumerated by morphology. Results are mean±SD of fibrocytes per $2.5 \times 10^5$ PBMC (n=3 separate experiments).

Serum amyloid P is a constitutive plasma protein and is closely related to CRP, the major acute phase protein in humans. To assess whether other plasma proteins could also inhibit the differentiation of fibrocytes, PBMC were cultured in serum-free medium in the presence of commercially available purified SAP, CRP, C4b or Protein S. The commercially available SAP was purified using calcium-dependent affinity chromatography on unsubstituted agarose. Of the proteins tested, only SAP was able to inhibit fibrocyte differentiation, with maximal inhibitory activity at 10 µg/ml (FIG. 4). A dilution curve indicated that the commercially available SAP has approximately $6.6 \times 10^3$ units/mg of activity (FIG. 4). Serum and plasma contain between 30-50 µg/ml SAP. Fibrocytes began to appear at a plasma dilution of 0.5%, which would be approximately 0.15-0.25 µg/ml SAP, which is comparable to the threshold concentration of purified SAP. The data showing that SAP purified using two different procedures inhibits fibrocyte differentiation strongly suggests that SAP inhibits fibrocyte differentiation.

Figure 5A:
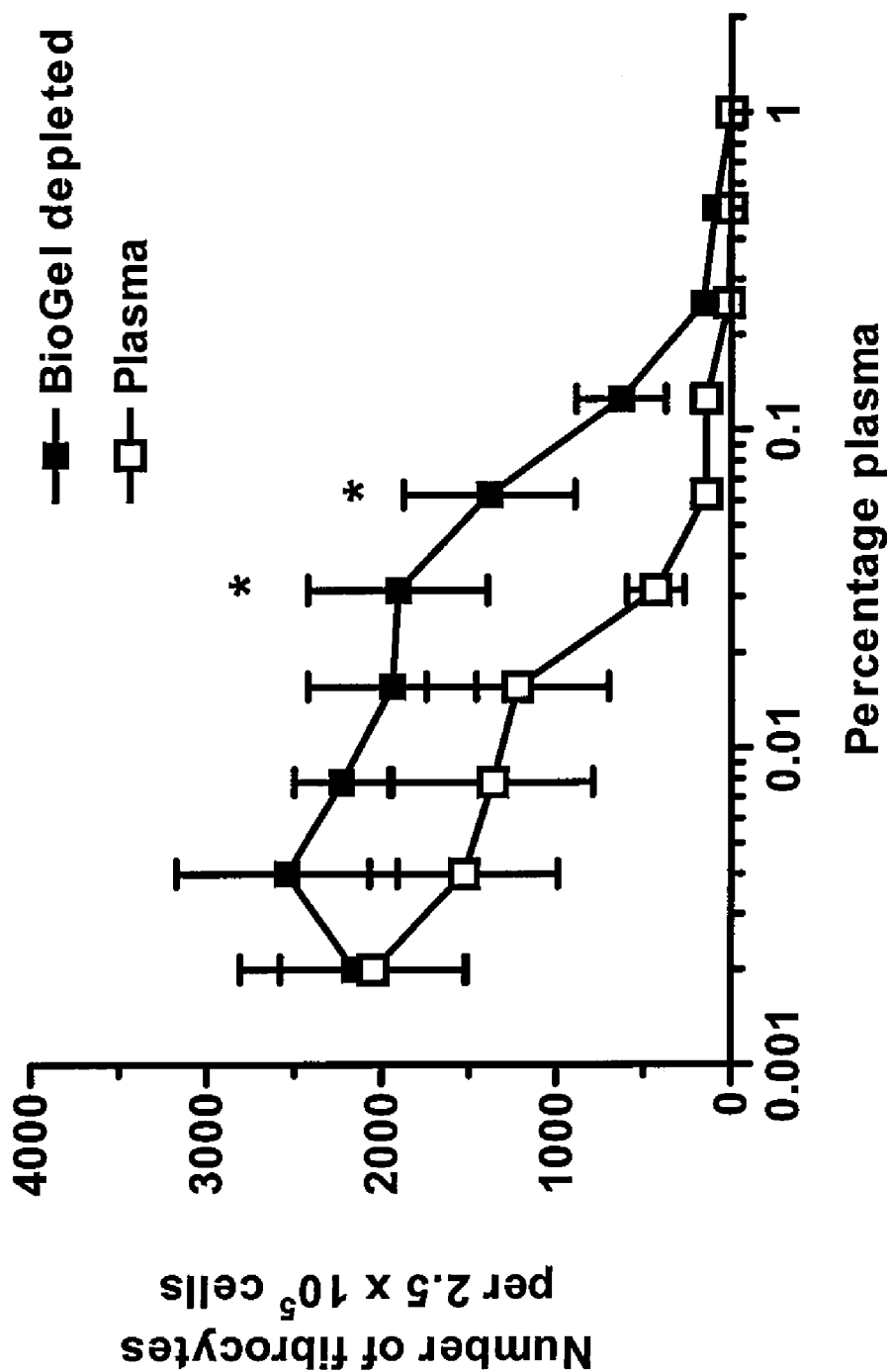
FIG. 5A shows the effect on fibrocyte differentiation of depleting SAP from plasma with BioGel agarose beads. Number of fibrocytes found in an assay supplied with either plasma (open square) or BioGel depleted plasma (filled square) at a variety of dilutions is shown. Stars indicate statistically significant differences between the two curves.

Although these data indicate that SAP is capable of inhibiting fibrocyte development and SAP purifies in a manner that indicates that it is the active factor in plasma, it was not determined whether depletion of SAP from plasma and serum would negate the inhibition. Accordingly, SAP was depleted from plasma using agarose beads (BioGel A, BioRad). Plasma was diluted to 20% in 100 mM Tris pH 8, 150 mM NaCl, 5 mM $CaCl_2$ buffer and mixed with 1 ml agarose beads for 2 hours at 4° C. Beads were then removed by centrifugation and the process repeated. This depleted plasma was then assessed for its ability to inhibit fibrocyte differentiation. The control plasma diluted to 20% in 100 mM Tris pH 8, 150 mM NaCl, 5 mM $CaCl_2$ buffer had a similar dilution curve to that observed with untreated plasma. In contrast, the bead-treated plasma was less able to inhibit fibrocyte differentiation at intermediate levels of plasma. These data, along with the ability of purified SAP to inhibit fibrocyte differentiation, strongly suggest that SAP is the active factor in serum and plasma that inhibits fibrocyte differentiation. (See FIG. 5).

Figure 5B:
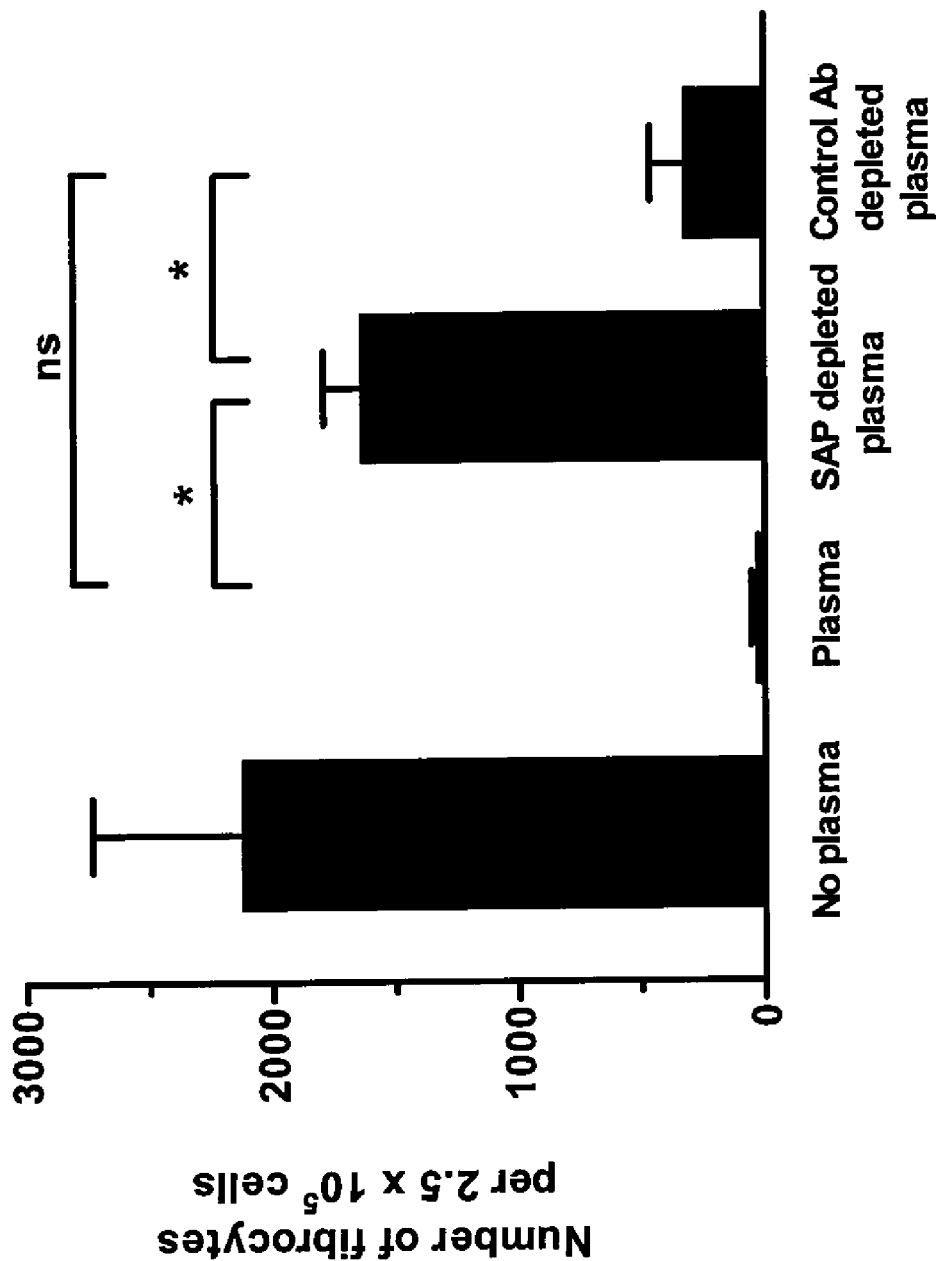
FIG. 5B shows the number of fibrocytes formed in an assay performed with no plasma or equal dilutions of plasma, BioGel SAP depleted plasma, or anti-SAP antibody depleted plasma. Stars indicate statistically significant differences.

Plasma was also depleted of SAP using protein G beads coated with anti-SAP antibodies. Removal of SAP led to a significant reduction in the ability of plasma to inhibit fibrocyte differentiation compared with plasma, or plasma treated with beads coated with control antibodies ($p<0.05$) (FIG. 5B). The beads coated with control antibodies did remove some of the fibrocyte-inhibitory activity from plasma, but this was not significantly different from cells cultured with plasma. This probably reflects SAP binding to the agarose in the protein G beads. These data, together with the ability of purified SAP to inhibit fibrocyte differentiation, strongly suggest that SAP is the active factor in serum and plasma that inhibits fibrocyte differentiation.

Example 5

Antibodies and Proteins

Purified human CRP, serum amyloid P, protein S and C4b were purchased from Calbiochem (San Diego, Calif.). Monoclonal antibodies to CD1a, CD3, CD11a, CD11b, CD11c, CD14, CD16, CD19, CD34, CD40, Pan CD45, CD64, CD83, CD90, HLA-DR/DP/DQ, mouse IgM, mouse IgG1 and mouse IgG2a were from BD Pharmingen (BD Biosciences, San Diego, Calif.). Chemokine receptor antibodies were purchased from R and D Systems (Minneapolis, Minn.). Rabbit anti-collagen I was from Chemicon International (Temecula, Calif.), monoclonal C4b-binding protein was from Green Mountain Antibodies (Burlington, VE), sheep anti human C4b-binding protein was from The Binding Site (Birmingham, UK), monoclonal anti-CRP was from Sigma (St. Louis, Mo.). Polyclonal rabbit anti-protein S was from Biogenesis (Poole, Dorset, UK).

Example 6

Cell Separation

Peripheral blood mononuclear cells were isolated from buffy coats (Gulf Coast Regional Blood Center, Houston, Tex.) by Ficoll-Paque (Amersham Biosciences, Piscataway, N.J., USA) centrifugation for 40 minutes at 400×g. Depletion of specified leukocyte subsets was performed using negative selection using magnetic Dynabeads (Dynal Biotech Inc., Lake Success, N.Y.). Briefly, PBMC were incubated with primary antibodies for 30 minutes at 4° C. Cells were then washed and incubated with Dynabeads coated with goat anti-mouse IgG for 30 minutes, before removal of antibody-coated cells by magnetic selection. This process was repeated twice. The negatively selected cells were routinely in excess of 98% pure as determined by monoclonal antibody labeling.

Example 7

Cell Culture and Fibrocyte Differentiation Assay

Cells were incubated in serum-free medium: RPMI (GibcoBRL Life, Invitrogen, Carlsbad, Calif., USA) supplemented with 10 mM HEPES (GibcoBRL/Life), 2 mM glutamine, 100 U/ml penicillin and 100 µg/ml streptomycin, 0.2% bovine serum albumin (BSA, Sigma), 5 µg/ml insulin (Sigma), 5 µg/ml iron-saturated transferrin (Sigma) and 5 ng/ml sodium selenite (Sigma). Normal human serum (Sigma), normal human plasma (Gulf Coast Regional Blood Center) or fetal calf serum (Sigma), column fractions, sera and synovial fluid from patients or purified proteins were added at the stated concentrations. Patient samples were obtained from a repository available to researchers at University of Texas Medical School at Houston. This repository keeps patient information confidential, and meets all NIH guidelines.

PBMC were cultured in 24 or 96 well tissue culture plates in 2 ml or 200 µl volumes respectively (Becton Dickinson, Franklin Lakes, N.J.) at $2.5 \times 10^5$ cells per ml in a humidified incubator containing 5% $CO_2$ at 37° C. for the indicated times. Fibrocytes in 5 different 900 µm diameter fields of view were enumerated by morphology in viable cultures as adherent cells with an elongated spindle-shaped morphology as distinct from small lymphocytes or adherent monocytes. Alternatively cells were air dried, fixed in methanol and stained with hematoxylin and methylene blue (Hema 3 Stain, VWR, Houston, Tex.). Fibrocytes were counted using the above criterion and the presence of an oval nucleus. Enumeration of fibrocytes was performed on cells cultured for 6 days in flat-bottomed 96 well plates, with $2.5 \times 10^4$ cells per well. In addition, fibrocyte identity was confirmed by immunoperoxidase staining (see below). The fibrocyte inhibitory activity of a sample was defined as the reciprocal of the dilution at which it inhibited fibrocyte differentiation by 50%, when added to serum-free medium.

Example 8

Purification and Characterization of Serum and Plasma Proteins 100 ml of frozen human serum or plasma was thawed rapidly at 37° C. and 1× "Complete" protease inhibitor (Roche, Indianapolis, Ind., USA), 1 mM benzamidine HCl (Sigma) and 1 mM Pefabloc (AEBSF: 4-(2-Aminoethyl)-benzenesulfonyl fluoride hydrochloride, Roche) were added. All subsequent steps were performed on ice or at 4° C. Barium citrate adsorption of plasma was performed as described previously. The precipitate was collected by centrifugation at 10,000×g for 15 minutes, resuspended in 20 ml of 100 mM $BaCl_2$ plus inhibitors and recentrifuged. After two rounds of washing, the pellet was resuspended to 20 ml in 10 mM sodium phosphate buffer pH 7.4 containing 5 mM EDTA and 1 mM benzamidine HCl and dialyzed for 24 hours against three changes of 4 liters of the same buffer.

Chromatography was performed using an Econo system (Bio-Rad, Hercules, Calif.) collecting 1 ml samples with a flow rate of 1 ml/min. The dialyzed barium citrate precipitate was loaded onto a 5 ml Hi-Trap Heparin column (Amersham Biosciences) and the column was washed extensively in 10 mM sodium phosphate buffer pH 7.4 until the absorbance at 280 nm returned to baseline. Bound material was eluted with a stepped gradient of 15 mls each of 100, 200, 300 and 500 mM NaCl in 10 mM sodium phosphate buffer pH 7.4. The fractions that inhibited monocyte to fibrocyte differentiation eluted at 200 mM NaCl. These were pooled (2 ml) and loaded onto a 5 ml Econo-Pak High Q column. After washing the column in 10 mM phosphate buffer, the bound material was eluted with the stepped gradient as above, with the active fraction eluting at 300 mM NaCl.

Active fractions from the High Q chromatography were concentrated to 200 µl using Aquacide II (Calbiochem) and then loaded onto a 4-20% native polyacrylamide gels (BMA, BioWhittaker, Rockland, Me.) as described previously. After electrophoresis, gel lanes were cut into 5 mm slices, mixed with 200 µl 20 mM sodium phosphate, 150 mM NaCl, 5 mM EDTA pH 7.4 containing 1 mM benzamidine HCl, crushed with a small pestle in an eppendorf tube and placed on an end-over-end mixer at 4° C. for 3 days. Proteins that eluted from the gel were analyzed for activity. To obtain amino acid sequences, proteins eluted from the gel slices were loaded onto a 4-20% gel with 100 µM thioglycolic acid in the upper chamber (Sigma). After electrophoresis the gel was rapidly stained with Coomasie brilliant blue, destained, and the bands excised off the gel. Amino acid sequencing was performed by Dr Richard Cook, Protein Sequencing Facility, Department of Immunology, Baylor College of Medicine.

Example 9

Western Blotting

For western blotting, plasma and serum samples were diluted 1:500 in 10 mM sodium phosphate pH 7.4. Fractions from heparin and High Q columns were not diluted. Samples were mixed with Laemmeli's sample buffer containing 20 mM DTT and heated to 100° C. for 5 minutes. Samples were loaded onto 4-20% Tris/glycine polyacrylamide gels (Cambrex). Samples for native gels were analyzed in the absence of DTT or SDS. Proteins were transferred to PVDF (Immobilon P, Millipore, Bedford, Mass.) membranes in Tris/glycine/SDS buffer containing 20% methanol. Filters were blocked with Tris buffered saline (TBS) pH 7.4 containing 5% BSA, 5% non-fat milk protein and 0.1% Tween 20 at 4° C. for 18 hours. Primary and biotinylated secondary antibodies were diluted in TBS pH 7.4 containing 5% BSA, 5% non-fat milk protein and 0.1% Tween 20 using pre-determined optimal dilutions (data not shown) for 60 minutes. ExtrAvidin-peroxidase (Sigma) diluted in TBS pH 7.4 containing 5% BSA and 0.1% Tween 20 was used to identify biotinylated antibody and chemiluminescence (ECL, Amersham Biosciences) was used to visualize the result.

Example 10

Immunohistochemistry

Cells cultured on 8 well glass microscope slides (Lab-Tek, Nalge Nunc International, Naperville, Ill.) were air dried before fixation in acetone for 15 minutes. Endogenous peroxidase was quenched for 15 minutes with 0.03% $H_2O_2$ and then non-specific binding was blocked by incubation in 2% BSA in PBS for 60 minutes. Slides were incubated with primary antibodies in PBS containing 2% BSA for 60 minutes. Isotype-matched irrelevant antibodies were used as controls. Slides were then washed in three changes of PBS over 15 minutes and incubated for 60 minutes with biotinylated goat anti-mouse Ig (BD Pharmingen). After washing, the biotinylated antibodies were detected by ExtrAvidin peroxidase (Sigma). Staining was developed with DAB (Diaminobenzadine, Sigma) for 3 minutes and counterstained for 30 seconds with Mayer's haemalum (Sigma).

Example 11

Expression of Surface Makers on Fibrocytes

PBMC were cultured in the wells of 8 well glass slides at $2.5 \times 10^5$ cells per ml (400 µl per well) in serum-free medium for 6 days. Cells were then air dried, fixed in acetone and stained by immunoperoxidase. Cells were scored positive or negative for the indicated antigens, compared to isotype-matched control antibodies.

Example 12

Recovery of Protein and Fibrocyte Inhibitory Activity from Fractionated Human Plasma Plasma was fractionated by $BaCl_2$ precipitation, heparin and ion exchange chromatography. Protein concentrations were assessed by spectrophotometry at 280 nm. Inhibition of fibrocyte differentiation was assessed by morphology. The fibrocyte inhibitory activity of a sample was defined as the reciprocal of the dilution at which it inhibited fibrocyte differentiation by 50%, when added to serum-free medium.

Example 13

IL-12

Figure 6A:
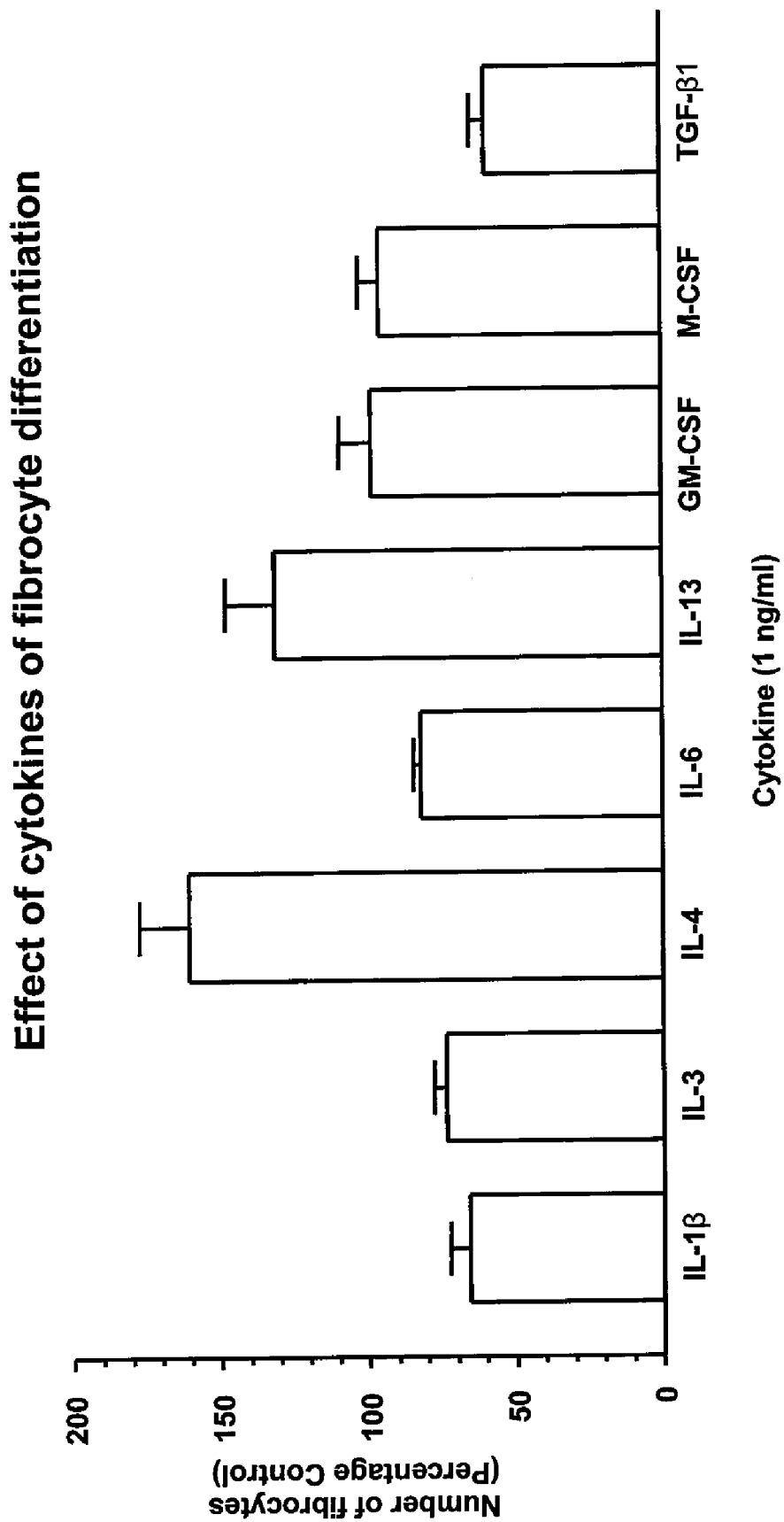
FIG. 6A shows the effects of a variety of cytokines.
Figure 6B:
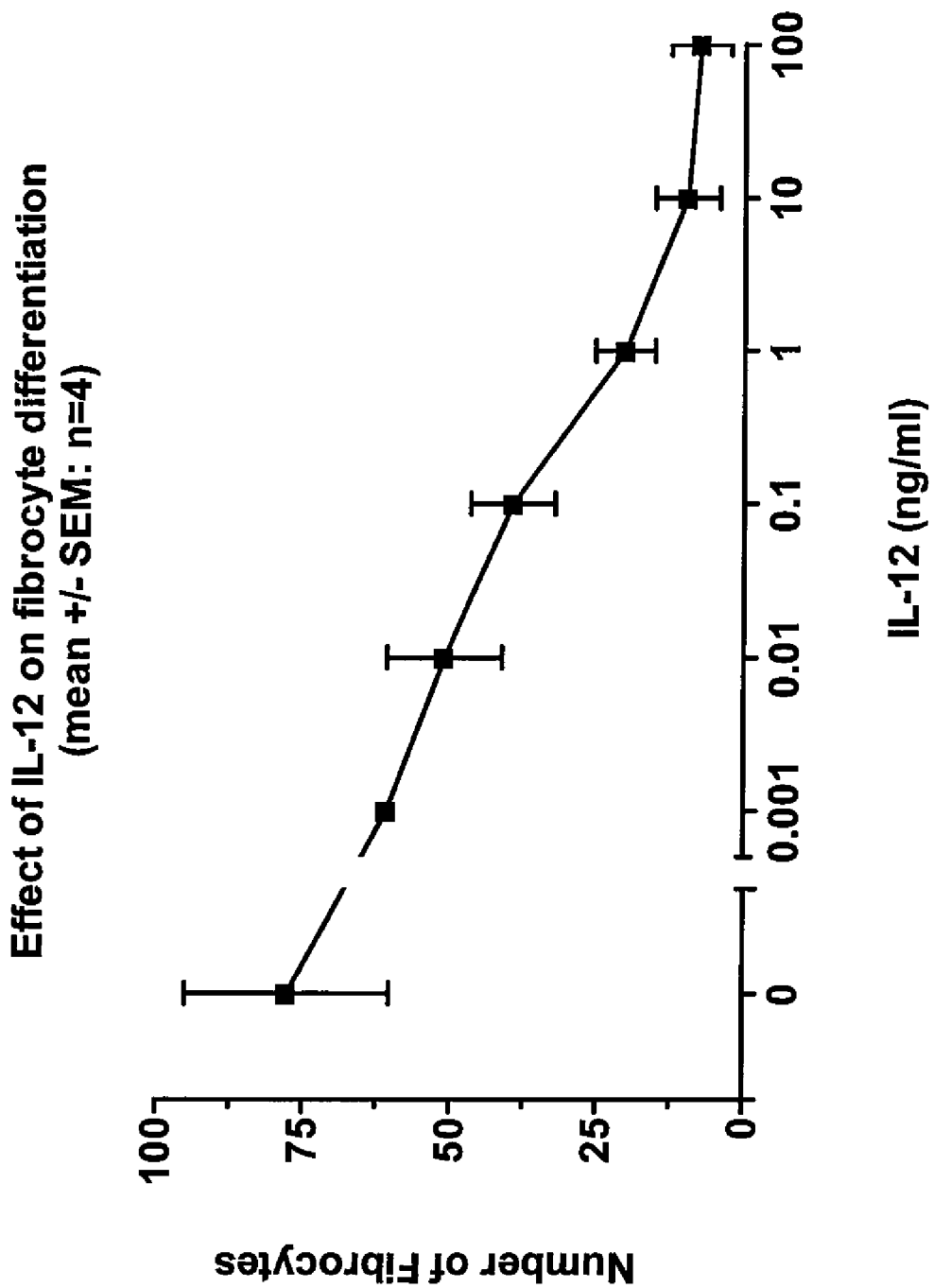
FIG. 6B shows the effects of IL-12 in greater detail.

Experiments have shown that IL-12 is capable of promoting fibrocyte differentiation in vitro. Specifically, peripheral blood mononuclear cells were cultured in serum-free medium in the presence of various cytokines (See FIG. 6A). Concentrations of IL-12 above approximately 5 ng/ml inhibited the number of fibrocytes in culture. (See FIG. 6B.) This indicates that IL-12 is capable of suppressing the differentiation of fibrocyte precursors into mature fibrocytes.

Example 14

Laminin-1

Figure 7A:
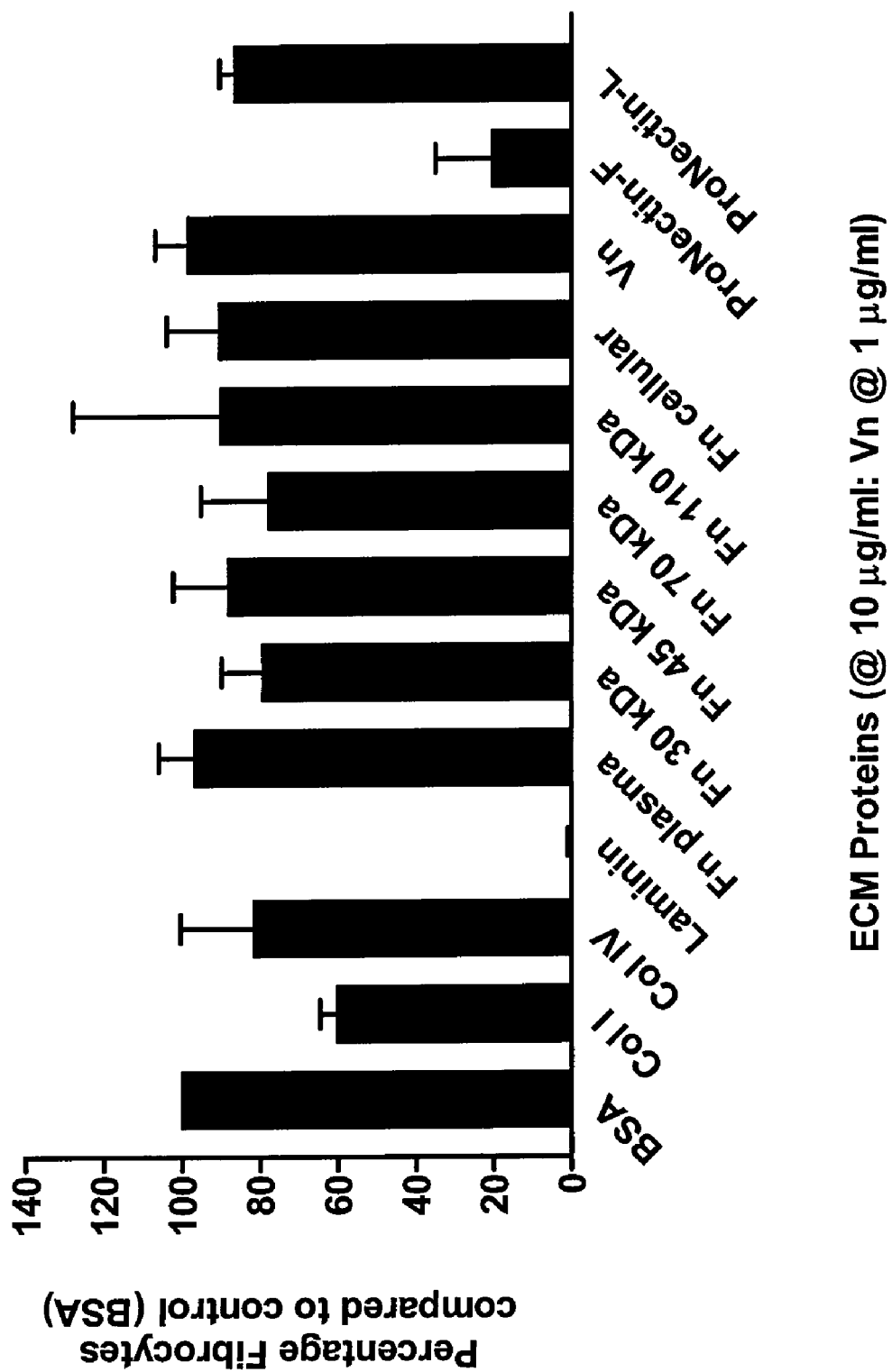
FIG. 7 shows the effects of extracellular matrix proteins on fibrocyte formation. Extracellular matrix proteins were bound to 96 well tissue culture plates for 18 hours at 4° C. in 50 mM carbonate buffer pH 9.5. ProNectin-F and ProNectin-L were diluted in PBS. Plates were washed in PBS, and incubated for 60 minutes at 37° C. in PBS containing 2% bovine serum albumin, to prevent non-specific binding. Plates were washed with PBS and then tissue culture medium. PBMC were then added and cultured for 4 days. Results for a variety of extracellular matrix proteins are shown in FIG. 7A. The effects of Laminin-1, Laminin-10/11 and ProNectin-L are shown in greater detail in FIG. 7B.

The process of crossing the endothelium and basement membrane induces activation and differentiation signals for monocytes. Therefore, experiments were performed to determine if extracellular matrix proteins had an effect on the differentiation of fibrocytes. Extracellular matrix proteins were bound to 96 well tissue culture plates for 18 hours at 4° C. in 50 mM carbonate buffer pH 9.5. ProNectin-F and ProNectin-L were diluted in PBS. Plates were washed in PBS, and incubated for 60 minutes at 37° C. in PBS containing 2% bovine serum albumin, to prevent non-specific binding. Plates were washed with PBS and then tissue culture medium. PBMC were then added and cultured for 4 days. Differentiation of fibrocytes was unaffected by culturing on a wide variety of ECM proteins, including collagens, fibronectin and vitronectin. However, culturing PBMC with either laminin-1 (Sigma-Aldrich, St. Louis, Mo.) or ProNectin-F (Sanyo Chemical Industries Inc, Kyoto, Japan) led to a significant reduction in the number of fibrocytes (See FIG. 7A) ($p<0.0001$). ProNectin-F is a construct of silk protein and repeats of the canonical RGD adhesion sequence from fibronectin. ProNectin-L is a similar construct to ProNectin-F, with the amino acid sequence IKVAV, from the α1 chain of laminin.

Figure 7B:
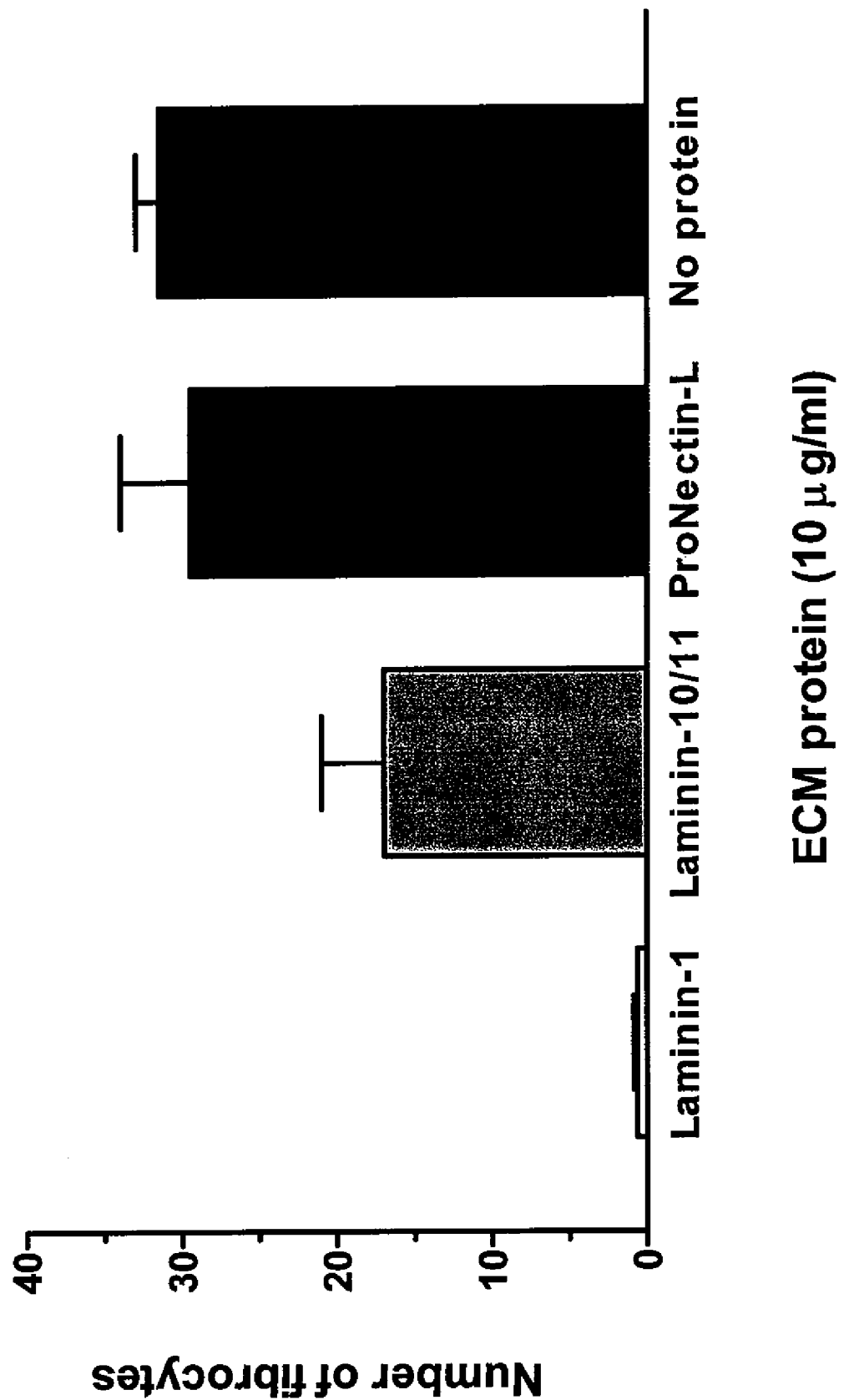

Additional experiments were performed to determine whether other laminin proteins could suppress fibrocyte differentiation. Laminin 10/11 (Chemicon, Temecula, Calif.) a second commercially available laminin, was not capable of inhibiting fibrocyte differentiation, compared to laminin-1. (See FIG. 7B) This data suggests that sequences specific to laminin-1, outside the IKVAV region, and absent from laminin-10 and -11, may be responsible for the suppressive effect on fibrocyte differentiation.

Example 15

Antibody Studies

Figure 8:
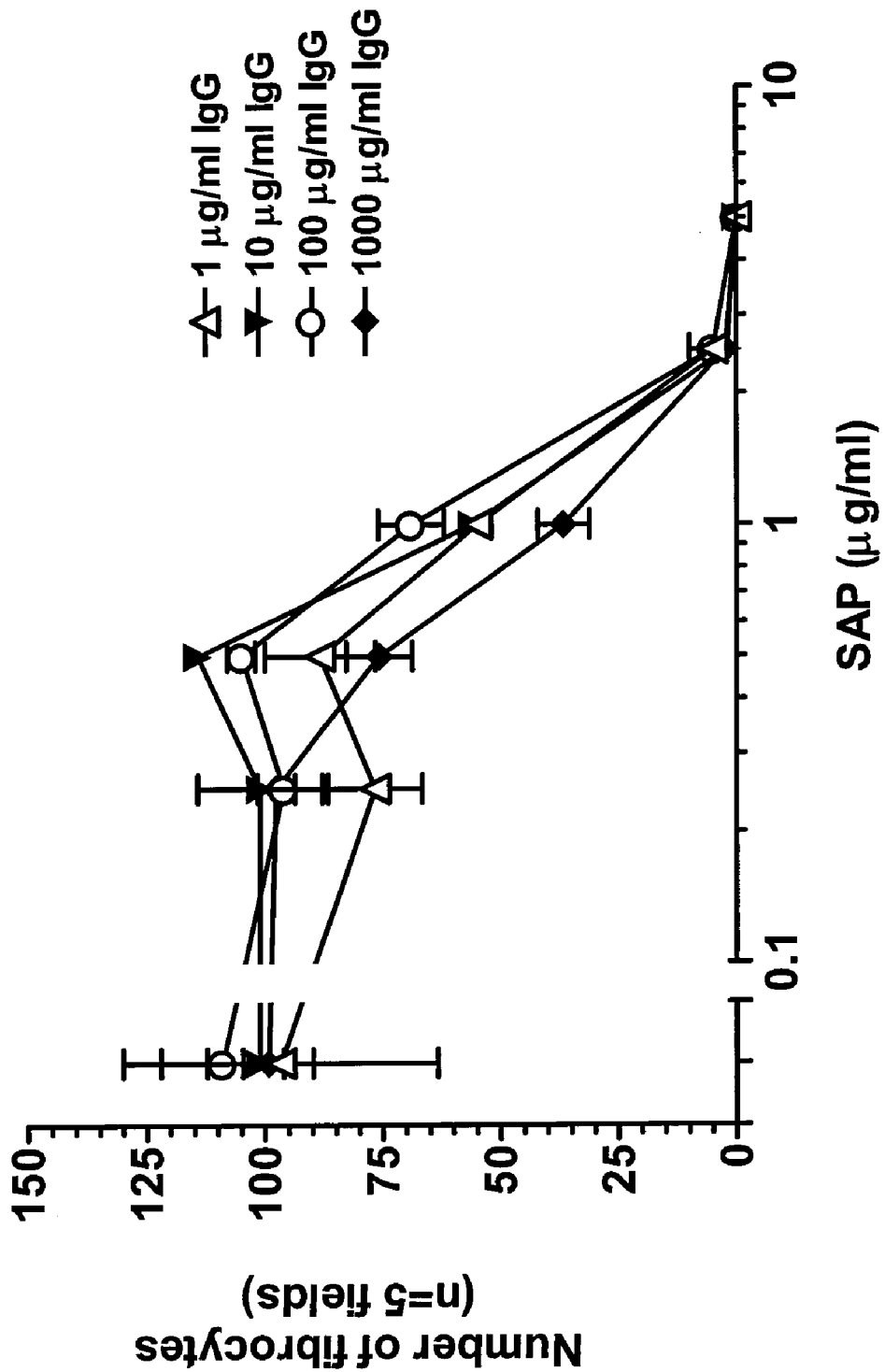
FIG. 8 shows the effects of monomeric IgG on the ability of SAP to bind to monocytes and inhibit their differentiation. PBMC were cultured in serum-free medium in the presence of a range of concentrations of monomeric IgG for 60 minutes. SAP, at the concentrations indicated, was then added and the cells were cultured for 4 days.

SAP and CRP augment phagocytosis and bind to Fcγ receptors on a variety of cells. CRP binds with a high affinity to FcγRII (CD32), a lower affinity to FcγRI (CD64), but does not bind FcγRIII (CD16). SAP binds to all three classical Fcγ receptors, with a preference for FcγRI and FcγRII. Monocytes constitutively express FcγRI. Because this receptor binds monomeric IgG, it is saturated in vivo. In order to determine whether the presence of monomeric human IgG could prevent SAP from inhibiting fibrocyte differentiation, PBMC were cultured in serum-free medium in the presence of a range of concentrations of monomeric IgG for 60 minutes. SAP, at the concentrations indicated in FIG. 8A, was then added and the cells were cultured for 4 days. As described in the above examples, 2.5 μg/ml SAP in the absence of IgG strongly inhibited fibrocyte differentiation. (See FIG. 8A.) Monomeric IgG in a range from 0.1 to 1000 μg/ml, which corresponds to approximately 0.001 to 10% serum respectively, had little effect on the suppression of fibrocyte formation by SAP.

Figure 9A:
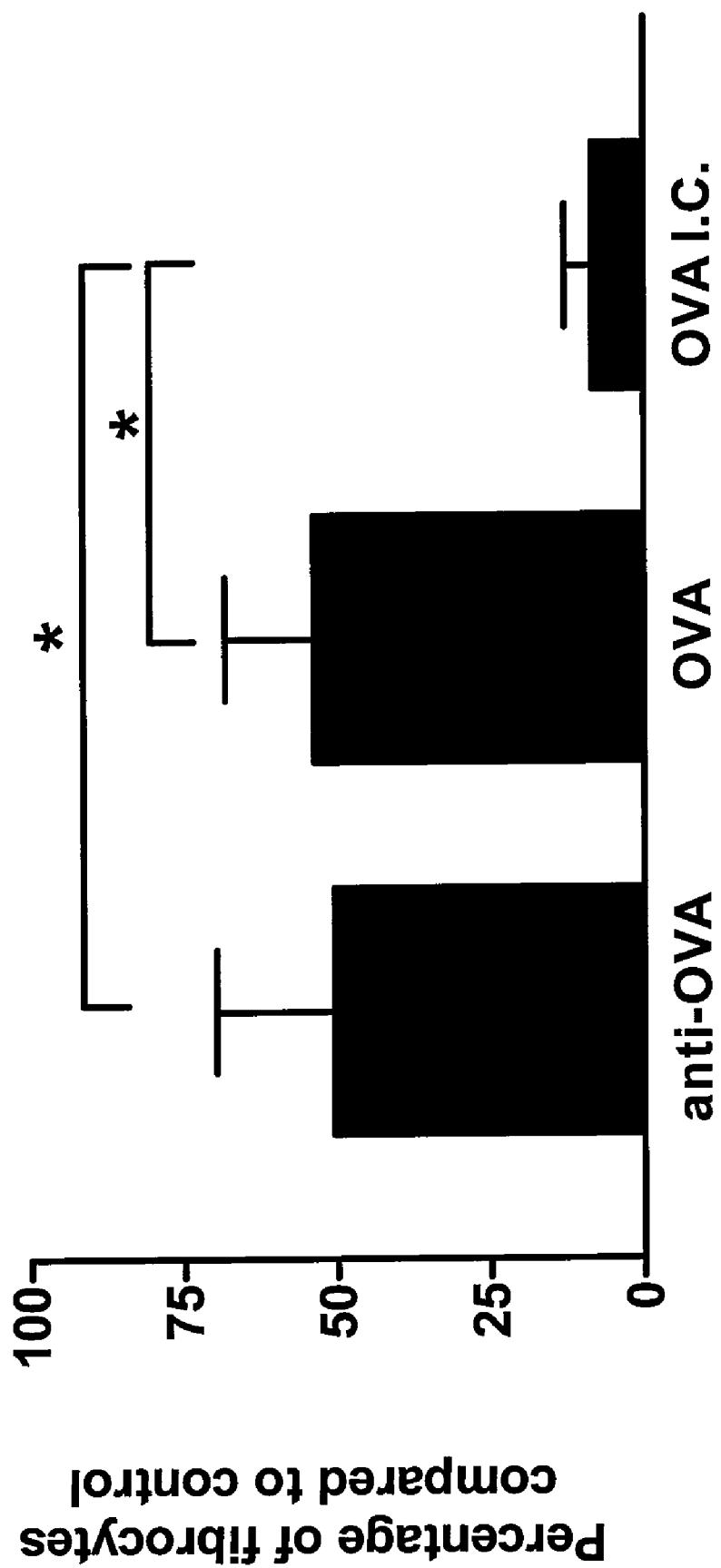
In FIG. 9A PBMC cultured for 4 days with ovalbumin or anti-ovalbumin mAb alone, or ovalbumin:anti-ovalbumin immune complexes.
Figure 9B:
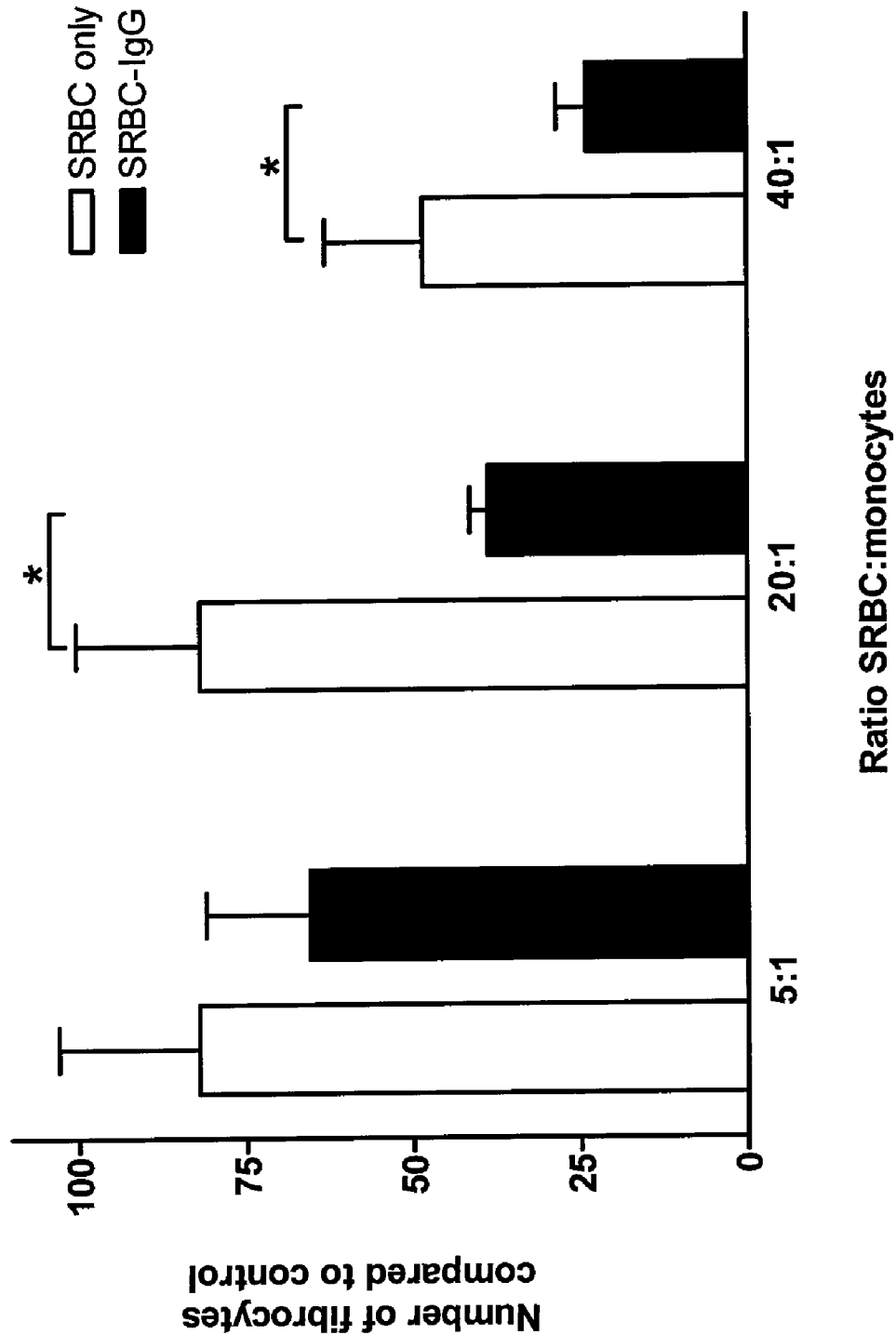
FIG. 9B shows the effects of SRBC alone and SRBC opsonised with rabbit anti-SRBC at 20:1 and 40:1 SRBC: monocyte ratios. Finally.
Figure 9C:
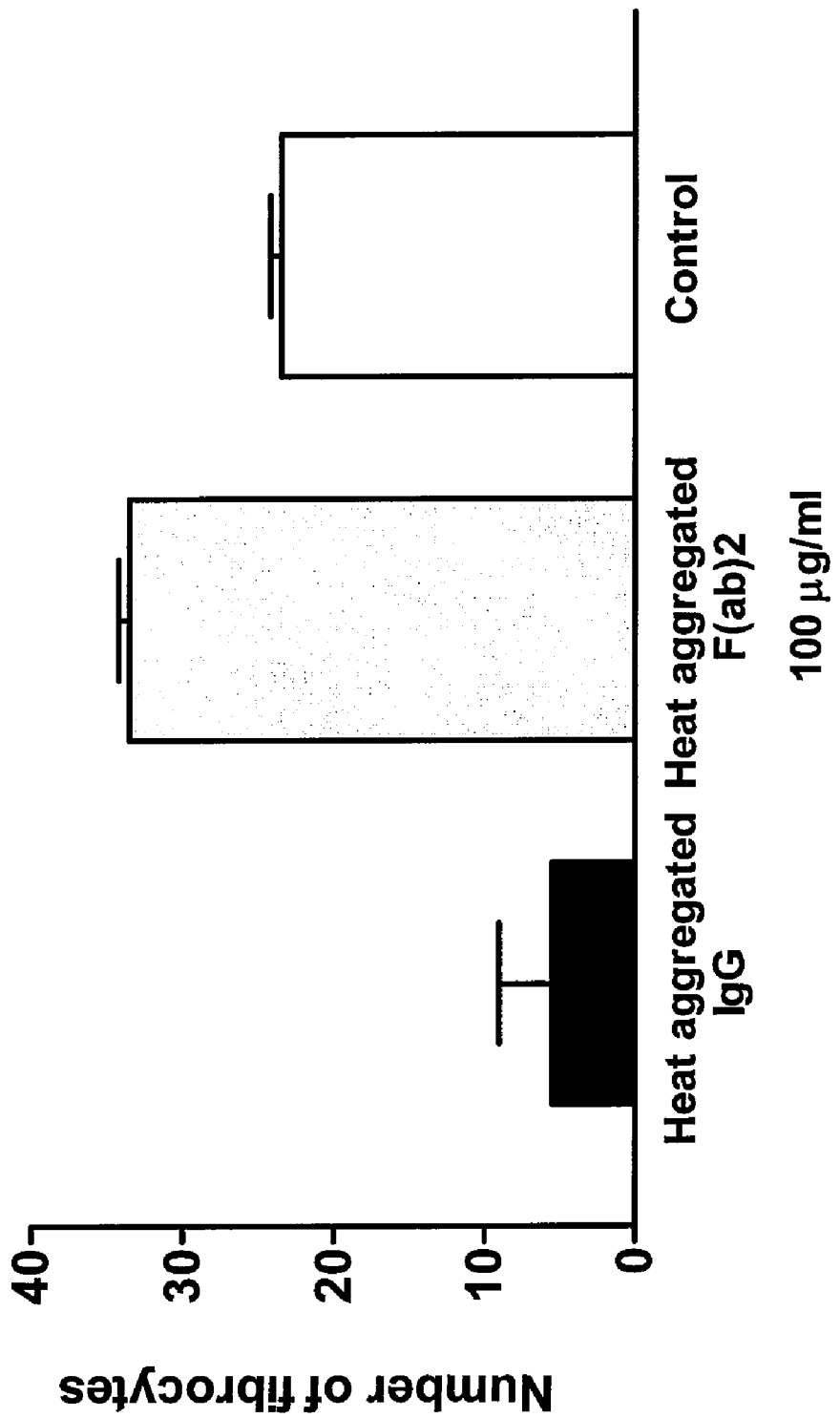
FIG. 9C shows the effects on PBMC of heat-aggregated IgG and heat-aggregated $F(ab)_2$. Stars in 9A and 9B indicate statistically significant differences.

To determine whether ligation and cross-linking of Fc receptors could also influence monocyte to fibrocyte differentiation, three test samples were used; soluble immune complexes (ovalbumin-antibody), particulate immune complexes, including opsonised SRBC and heat-aggregated IgG. PBMC cultured for 4 days with ovalbumin or anti-ovalbumin mAb showed that the two proteins alone had a modest effect on the differentiation of monocytes compared to cultures where no reagent was added. (See FIG. 9A.) However, the addition of ovalbumin:anti-ovalbumin immune complexes led to a significant reduction in the number of differentiated fibrocytes (See FIG. 9A). A similar effect was observed when PBMC were cultured with opsonised SRBC. SRBC opsonised with rabbit anti-SRBC at 20:1 and 40:1 SRBC:monocyte ratios significantly suppressed fibrocyte differentiation as compared to cells cultured with SRBC alone (See FIG. 9B). Finally, PBMC cultured with heat-aggregated IgG, but not heat-aggregated F(ab)$_2$, also showed potent inhibition of fibrocyte differentiation (See FIG. 9C.) Together these data suggest that ligation and cross-linking linking of Fc receptors is suppressor of monocyte to fibrocyte differentiation.

Figure 10:
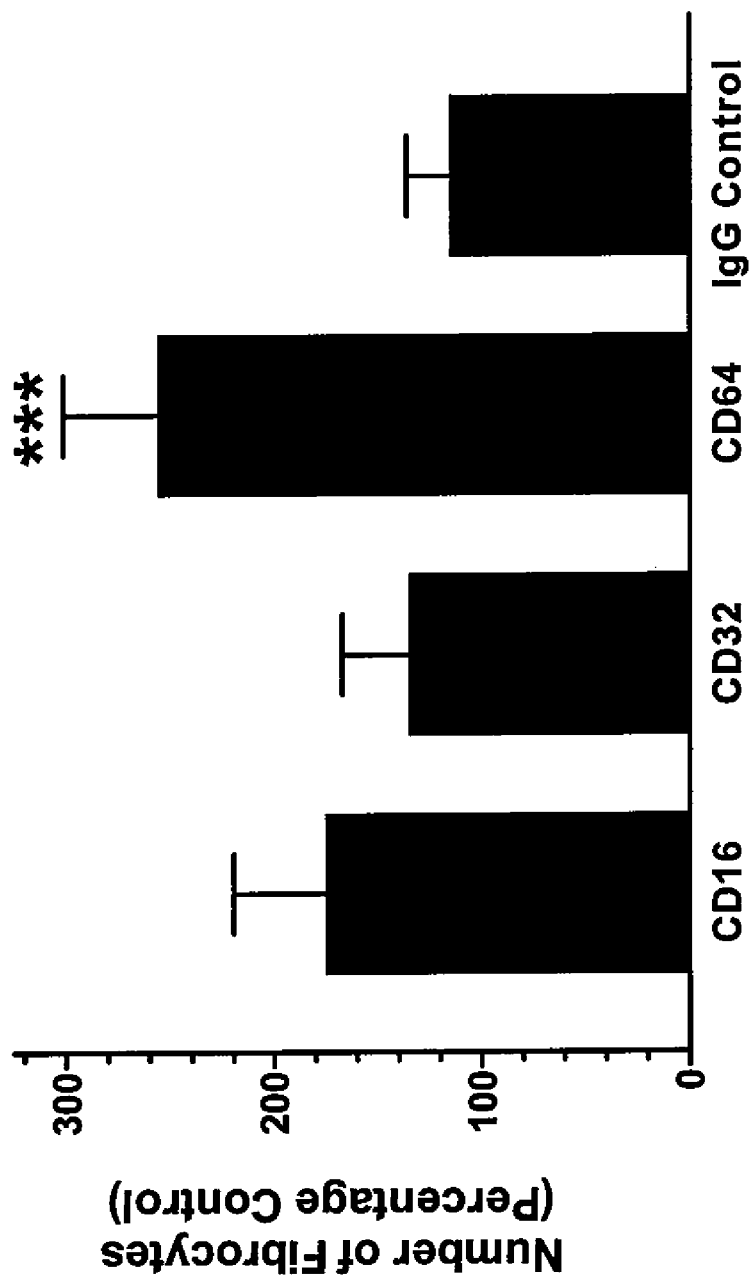
FIG. 10 shows the effects of anti-FcγR antibodies on monocyte differentiation. Stars indicate a statistically significant difference from control.

The observation that immune complexes inhibit fibrocyte differentiation suggests that one or more FcγR influences fibrocyte differentiation. To examine the role of FcγR in fibrocyte differentiation PBMC were cultured in the presence or absence of blocking antibodies to FcγRI (CD64), FcγRII (CD32) or FcγRIII (CD16) before the addition of SAP, or as a control CRP. When samples were pre-incubated with a blocking mAb for each of the three FcγR, SAP was later able to modestly suppress fibrocyte differentiation. However, in the absence of exogenously added SAP, the FcγRI (CD64) blocking mAb had a profound effect on fibrocyte differentiation. Incubation of PBMC with blocking mAb to FcγRI, but not FcγRII or FcγRIII, promoted fibrocyte differentiation as compared to cells cultured with isotype-matched control mAb or cells cultured with no mAb ($P<0.01$) (See FIG. 10). These data suggested that SAP or IgG, might have been produced by some cells in the culture system over 4 days, or that SAP or IgG was retained by cells from the blood. Western blotting failed to show the presence of SAP or IgG after cells had been cultured for 4 days in vitro. This suggests that the FcγRI blocking mAb has a direct effect on fibrocyte differentiation or that SAP or IgG were only present during the early time points of the cell culture.

Example 16

Pulmonary Fibrosis

To determine the effects of SAP in treatment of a fibrosing disease, pulmonary fibrosis was selected as a model. Pulmonary fibrosis was induced in rats (Sprague Dawley, containing surgically implanted jugular cathethers, Charles River Laboratories, Wilmington, Mass.) by injection of bleomycin into their lungs. Bleomycin is an antineoplastic agent that, when injected into the airway, causes fibrosis in the lungs of an animal. It is a standard way to study lung fibrosis. (Crouch, E. 1990. Pathobiology of pulmonary fibrosis. Am J Physiol Lung Cell Mol Physiol 259:L159-L184.)

To induce fibrosis, rats were anesthetized by 4% isoflurane, maintained with 2.5% isoflurane by non-rebreather mask, and monitored to ensure an appropriate surgical plane of anesthesia was achieved and maintained. The ventral side of the neck was shaved and disinfected with an ethanol/iodine solution. A vertical midline incision was made in the ventral side of the neck, the neck muscles were retracted, and the trachea was exposed. 300 microliters of a 3.3 U/ml solution (1 unit) of bleomycin (Calbiochem/EMD Biosciences, San Diego, Calif.) in sterile 0.9% saline was injected with a syringe and a 26-gauge needle into the lumen of the trachea. Control rats had saline injected. The incision was closed with two or three sutures. This procedure follows that published by Underwood et al. (2000. SB 239063, a p38 MAPK inhibitor, reduces neutrophilia, inflammatory cytokines, MMP-9, and fibrosis in lung. Am J Physiol Lung Cell Mol Physiol 279:L895-L902.) During the procedure and postoperatively the animal was maintained under a heating lamp, and then placed back in its cage once it had fully recovered. During the procedure the animal was checked to ensure it was: i) was breathing regularly, ii) had pink ears and mucous membranes, iii) did not withdraw its foot when its toes were pinched, and iv) did not blink when the eye or eyelid was touched.

Native rat SAP was isolated from commercially available rat serum (Gemini BioProducts, Woodland, Calif.). To purify the rat SAP, published purification techniques using calcium-dependent binding to phosphoethanolamine-conjugated agarose were followed. (de Beer, F. C., M. L. Baltz, E. A. Munn, A. Feinstein, J. Taylor, C. Bruton, J. R. Clamp, and M. B. Pepys. 1982. Isolation and characterization of C-reactive protein and serum amyloid P component in the rat. Immunology 45:55-70; Pepys, M. B., D. R. Booth, W. L. Hutchinson, J. R. Gallimore, P. M. Collins, and E. Hohenester. 1997. Amyloid P component. A critical review. Amyloid. 4:274-295.) Both native and SDS-polyacrylamide gel electrophoresis were used to assay the purity of the preparation. Before each experiment, the monocyte to fibrocyte differentiation inhibiting activity of the SAP preparation was assayed using rat monocytes. To avoid contamination of the rat SAP that was used for injection, pyrogen-free solutions and sterile plasticware and tubing were used for the preparation. Endotoxin levels were tested using the a Limulus amebocyte lysate assay kit (E-Toxate, Sigma-Aldrich, St. Louis, Mo. There were no contaminated preparations.

Some of the rats were injected with purified rat SAP intravenously via a jugular catheter implanted by the vendor. The protein was formulated in physiological saline (0.9% NaCl) and passed through a 0.2 micron filter before administration. The dose was 240 micrograms in 0.1 milliliter and was administered five times over the course of 9 days. This SAP injection schedule does not affect weight gain, respiration, pulse oximetry, spleen mass, or the appearance of organs at autopsy.

Every two days all the rats were weighed and ~100 μl of blood was collected from the jugular cannula. Serum was used to verify that the injections had increased serum SAP levels by monitoring levels of rat SAP. Serum SAP levels were assayed by western blots (Polyclonal anti-rat SAP, R and D Systems). The first group of four rats was the control, and the second group of four rats were injected with 240 μg of purified rat SAP via the jugular cannula every two days beginning on day 1 after weighing and taking a blood sample. The third group of four had lung fibroses induced by bleomycin treatment on day 0, and were injected with saline via the jugular cannula every two days after removing the blood sample. The fourth group was injected via the jugular cannula, like group 2, with 240 μg of purified rat SAP every two days beginning on day 1 and had lung fibrosis induced with bleomycin on day 0. The rats weighed approximately 150 g each. Thus, approximately 1.6 μg/g was administered in each dose. A 150 g rat normally has approximately 8 ml of serum with a SAP concentration of approximately 30 μg/ml. Accordingly, a 240 μg dose approximately doubled the serum concentration of SAP. The animals were sacrificed on day 14. The injection schedule for each group of rats is provided in Table 3.

TABLE 3

Injection Schedule for Four Groups of Rats

| Group | Day 0 | Day 1 | Day 3 | Day 5 | Day 7 | Day 9 | Day 14 |
|---|---|---|---|---|---|---|---|
| 1 | Saline into lungs | Inject saline | Inject saline | Inject saline | Inject saline | Inject saline | sacrifice |
| 2 | Saline into lungs | Inject SAP | Inject SAP | Inject SAP | Inject SAP | Inject SAP | sacrifice |

TABLE 3-continued

Injection Schedule for Four Groups of Rats

| Group | Day 0 | Day 1 | Day 3 | Day 5 | Day 7 | Day 9 | Day 14 |
|---|---|---|---|---|---|---|---|
| 3 | Bleomycin into lungs | Inject saline | Inject saline | Inject saline | Inject saline | Inject saline | sacrifice |
| 4 | Bleomycin into lungs | Inject SAP | Inject SAP | Inject SAP | Inject SAP | Inject SAP | sacrifice |

Figure 11:
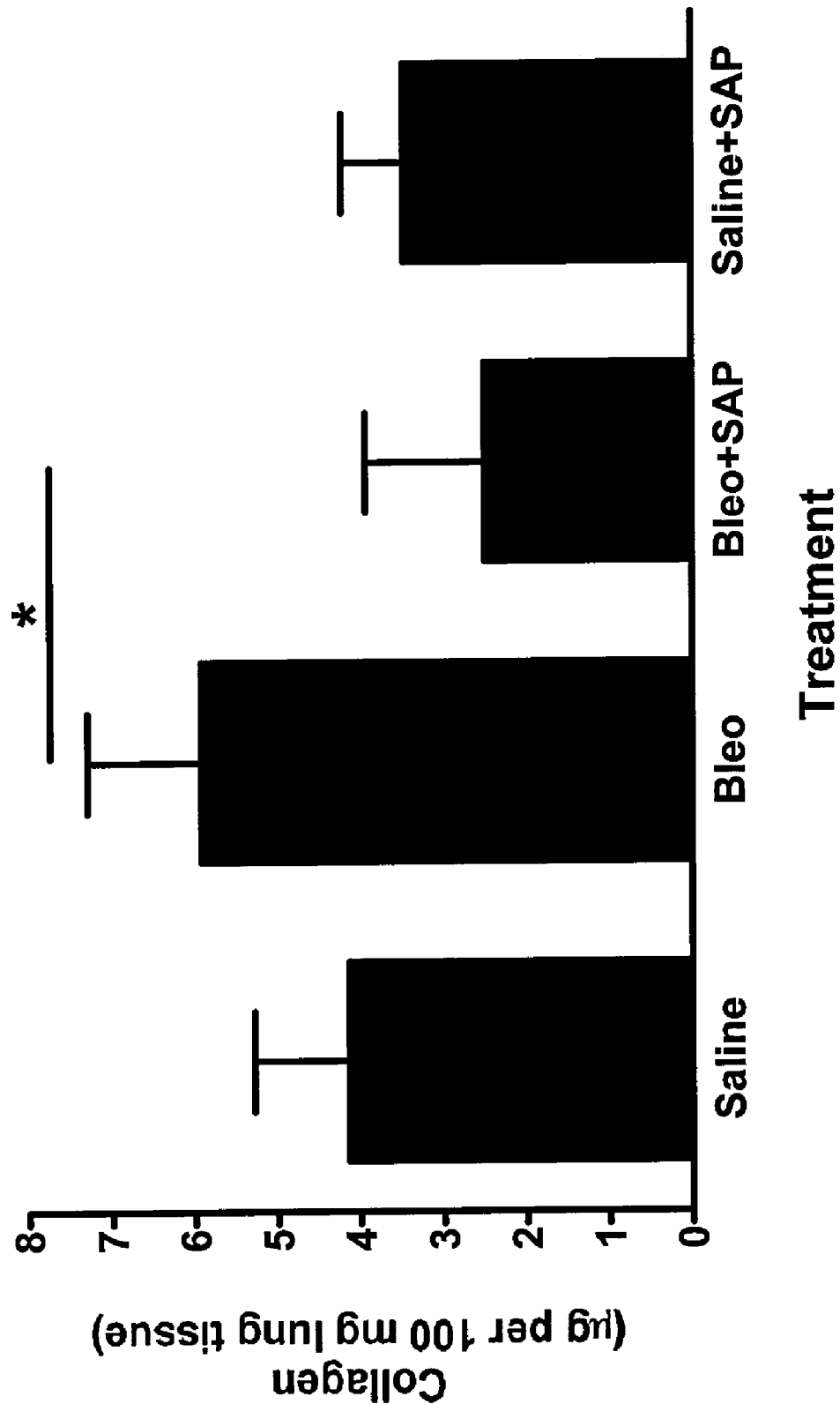
FIG. 11 shows the effects of SAP on collagen content in rat lungs. Intra-tracheal injection of bleomycin (Bleo) was used to induce fibrosis. Control rats had saline injected into their tracheas. "+SAP" indicates that rats were given an intravenous injection of 240 µg of rat SAP on days 1, 3, 5, 7 and 9. The animals were euthanized on day 14. Lung tissues were removed and homogenized then assayed for collagen content. Values are means+/−SEM (n=4). * indicates p<0.05 as determined by ANOVA.

Following euthanasia, lungs were perfused with phosphate-buffered saline to remove blood. One lung was weighed and homogenized. An aliquot of the homogenate was used to measure collagen using the Sircol collagen assay (Newtonabbey, NI, UK). These collagen measurements are summarized in FIG. 11. Specifically, collagen content in the lungs of rats administered bleomycin alone was quite high compared to that of rats administered only saline (normal). In contrast, rats administered bleomycin and SAP showed far less collagen than rats that received bleomycin, indicating that SAP helps prevent the development of fibrosis in the lungs and the accompanying accumulation of collagen.

Also of interest, SAP alone may also decrease collagen as compared to normal. This indicates that SAP may also have the potential to treat existing fibrosis by reducing collagen.

Tissue from the other lung was embedded in OCT (Sakura Finetek, Torrance, Calif.) and frozen. Cryosections were mounted on Superfrost Plus (VWR, West Chester, Pa.) slides. Cryosections were stained for collagen with Picrosirius red (Polysciences Inc., Warrington, Pa.), at 1 mg/ml in saturated picric acid. (Junqueira, L. C., G. Bignolas, and R. R. Brentani. 1979. Picrosirius staining plus polarization microscopy, a specific method for collagen detection in tissue sections. Histochem. J 11:447-455.) Fibrosis was assessed using a modified Ashcroft scale, where 0 is normal lung and 4 is severe distortion of the lung structure, with large fibrotic areas. (Ashcroft, T., J. M. Simpson, and V. Timbrell. 1988. Simple method of estimating severity of pulmonary fibrosis on a numerical scale. J Clin Pathol 41:467-470.) Using a 4× objective, 10 random fields were counted from lung sections taken from the top, middle and lower portions of each lung.

Figures 12A, 12B, 12C:
FIG. 12A shows a cryosection of a saline-treated rat lung 14 days after treatment began.
FIG. 12B shows a cryosection of a bleomycin-treated rat lung 14 days after treatment began.
FIG. 12C shows a cryosection of a SAP-treated rat lung also treated with bleomycin 14 days after treatment began. The rat was injected with 240 µg of purified rat SAP every 2 days for 9 days, starting the day after bleomycin treatment. All three sections were stained with Picrosirius red to label collagen. Bar is 0.5 mm.

Sample lung sections are provided in FIG. 12. FIG. 12A shows the cross section of lung from a rat in group 1. This lung section has a lacy pattern of cells characteristic of a normal lung. FIG. 12B shows the cross section of lung from a rat in group 3, which received bleomycin, but did not receive any SAP. This section shows that the lung has filled with cells and contains deposits of collagen which stain dark. This pattern is typical of rats and mice treated with bleomycin and also fibrotic human lungs. In contrast, FIG. 12C shows the cross section of a lung from a rat in group 4. This rat received bleomycin, but also received SAP. As a result of the SAP, this lung retained a very normal lacy appearance. There is no filling with cells and only a few, small collagen foci of collagen deposition. Thus, the administration of SAP appears to have prevented the development of pulmonary fibrosis in rats.

Figure 13:
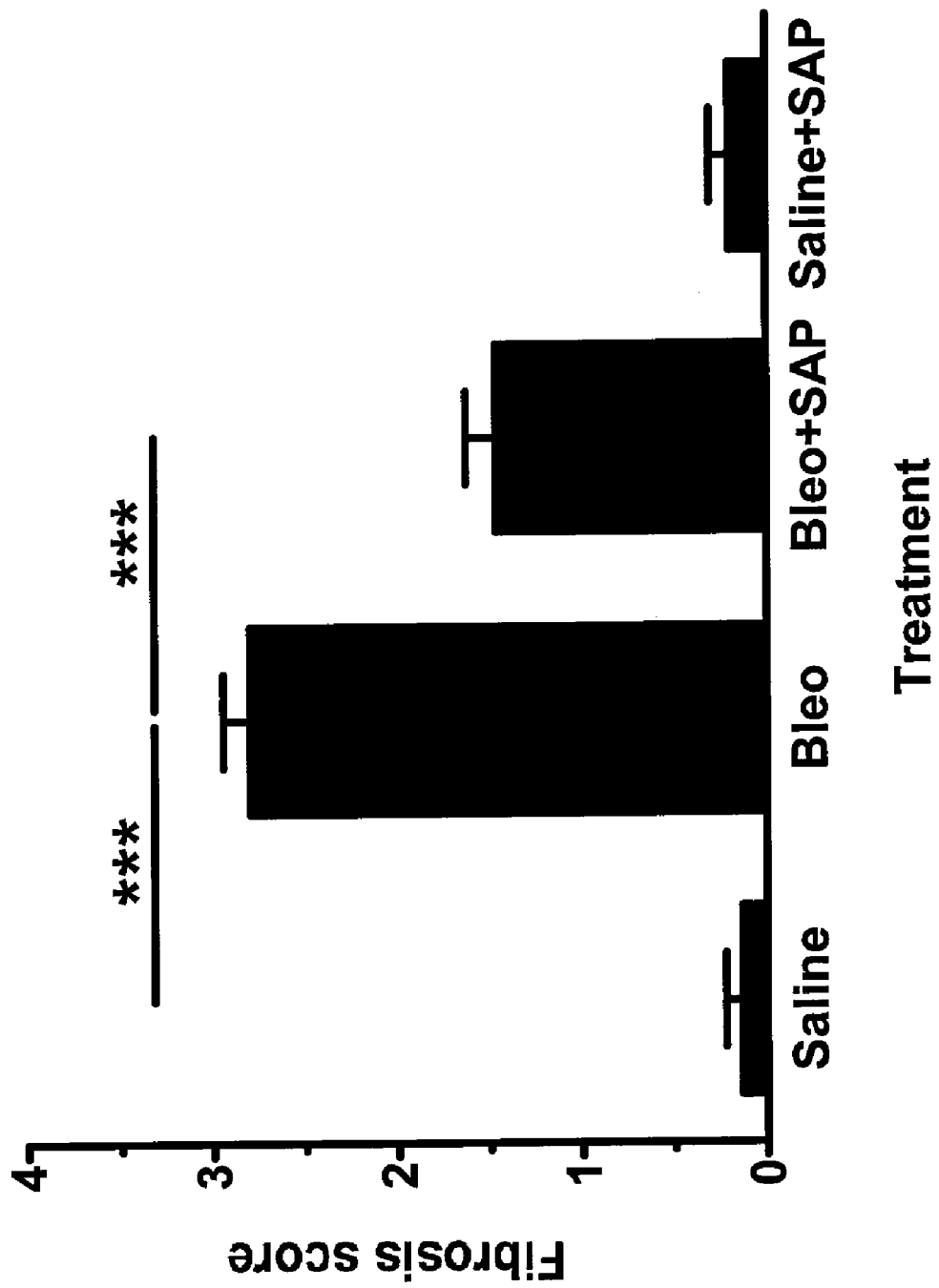
FIG. 13 shows the effects of SAP on fibrosis in rat lungs. Intra-tracheal injection of bleomycin (Bleo) was used to induce fibrosis. Control rats had saline injected into their tracheas. "+SAP" indicates that rats were given an intravenous injection of 240 µg of rat SAP on days 1, 3, 5, 7 and 9. The animals were euthanized on day 14. Lung tissues were removed and fibrosis was assessed using a modified Ashcroft score containing 5 fields per section, and from three separate areas of lung. Zero is a normal lung, 1 is minimal thickening of the alveolar wall, 2 and 3 are increased levels of fibrosis, and 4 is severe distortion of the lung structure with large areas of fibrosis. Values are means+/−SEM (n=4). *** indicates p<0.001 as determined by ANOVA.

FIG. 13 summarizes the lung section data for all four groups of rats. Rats receiving bleomycin had a very high fibrosis score using a modified Ashcroft score as compared to rats receiving saline only (normal). This fibrosis score was halved by the co-administration of SAP with bleomycin, demonstrating the ability of SAP to inhibit pulmonary fibrosis.

Not surprisingly, given the degree of lung fibrosis induced by bleomycin, animals treated with this agent had reduced oxygen content in their blood, and lost weight over the course of the two weeks of observation. Both symptoms of poor lung function were normalized by the SAP treatment. Such secondary effects provide convenient measures of utility that can be measured non-invasively and are thus useful in defining a clinical profile of SAP as a therapeutic agent.

Although only exemplary embodiments of the invention are specifically described above, it will be appreciated that modifications and variations of these examples are possible without departing from the spirit and intended scope of the invention.

The invention claimed is:

1. A method of suppressing fibrocyte formation in a mammal suffering from pulmonary fibrosis, the method comprising administering to a mammal in need thereof an amount of Serum Amyloid P (SAP) protein, or portion thereof, said portion comprising one or more sequences selected from the group consisting of SEQ ID NO:1, SEQ ID NO:2, and SEQ ID NO:3 sufficient to suppress pulmonary fibrosis, wherein the SAP or portion thereof binds to Fcγ receptors and inhibits fibrocyte differentiation from monocytes.

2. The method of claim 1, wherein the SAP or portion thereof has a concentration in the composition of at least approximately 0.5 μg/ml.

3. The method of claim 1, wherein administering the composition comprises administering by intravenous injection.

4. The method of claim 1, wherein the mammal is a human.

5. The method of claim 1, wherein said SAP or a portion thereof is conjugated to a biocompatible polymer.

6. The method of claim 5, wherein the biocompatible polymer is selected from the group consisting of PEG, a poly (amino acid), and a polysaccharide; or copolymers and combinations thereof.

7. The method of claim 1, further comprising administering a composition selected from the group consisting of IL-12, Laminin-1, IgG aggregates, cross-linked IgG and combinations thereof.

8. The method of claim 1, wherein administering comprises administering approximately 1.6 μg SAP or a portion thereof per gram of bodyweight of the mammal.

9. The method of claim 1, wherein administering comprises administering an amount of SAP or a portion thereof sufficient to approximately double the normal serum concentration of SAP or a portion thereof similar to the portion thereof administered in the mammal.

10. The method of claim 1, wherein administering comprises administering an amount of SAP sufficient to increases the normal serum concentration of SAP or the a portion thereof similar to the portion thereof administered in the mammal by approximately 25%.

11. The method of claim 1, wherein the SAP protein or a portion thereof forms a pentamer.

12. The method of claim 1, wherein administering comprises administering the SAP protein or a portion thereof an amount of approximately 600 µg or more.

13. The method of claim 1, wherein pulmonary fibrosis comprises a condition selected from the group consisting of: Adalimumab-associated pulmonary fibrosis, pulmonary interstitial fibrosis, sarcoidosis, idiopathic pulmonary fibrosis, asthma, chronic obstructive pulmonary disease, diffuse alveolar damage disease, pulmonary hypertension, neonatal bronchopulmonary dysplasia, and emphysema.

* * * * *

```
SEQUENCE LISTING

<160> NUMBER OF SEQ ID NOS: 8

<210> SEQ ID NO 1
<211> LENGTH: 25
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein regions
      that are not homolgous to CRP.

<400> SEQUENCE: 1

Lys Glu Arg Val Gly Glu Tyr Ser Leu Tyr Ile Gly Arg His Lys Val
 1               5                  10                  15

Thr Ser Lys Val Ile Glu Lys Phe Pro
            20                  25

<210> SEQ ID NO 2
<211> LENGTH: 12
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein regions
      that are not homolgous to CRP.

<400> SEQUENCE: 2

Ile Leu Ser Ala Tyr Gln Gly Thr Pro Leu Pro Ala
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein regions
      that are not homolgous to CRP.

<400> SEQUENCE: 3

Ile Arg Gly Tyr Val Ile Ile Lys Pro Leu Val
 1               5                  10

<210> SEQ ID NO 4
<211> LENGTH: 6
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein.

<400> SEQUENCE: 4

Val Phe Val Phe Pro Arg
 1               5

<210> SEQ ID NO 5
```

```
-continued

<211> LENGTH: 10
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein.

<400> SEQUENCE: 5

Val Gly Glu Tyr Ser Leu Tyr Ile Gly Arg
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein.

<400> SEQUENCE: 6

Ala Tyr Ser Leu Phe Ser Tyr Asn Thr Gln Gly Arg
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein.

<400> SEQUENCE: 7

Gln Gly Tyr Phe Val Glu Ala Gln Pro Lys
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein.

<400> SEQUENCE: 8

Ile Val Leu Gly Gln Glu Gln Asp Ser Tyr Gly Gly Lys
 1               5                  10
```